(12) United States Patent
Lea et al.

(10) Patent No.: US 11,331,349 B2
(45) Date of Patent: May 17, 2022

(54) TREATMENT OR PREVENTION OF GASTROINTESTINAL DYSBIOSIS

(71) Applicants: NORGES MILJO-OG BIOVITENSKAPELIGE UNIVERSITET (NMBU), As (NO); SYKEHUSET OSTFOLD HF, Gralum (NO); UNIVERSITY OF COPENHAGEN, Copenhagen (DK)

(72) Inventors: Tor Lea, Oslo (NO); Charlotte Kleiveland, Vestby (NO); Karsten Kristiansen, Broby (DK); Benjamin Anderschou Holbech Jensen, Quebec (CA); Jacob Bak Holm, Copenhagen (DK); Ida Sogaard Larsen, Quebec (CA); Morten Jacobsen, Moss (NO)

(73) Assignees: NORGES MILJO-OG BIOVITENSKAPELIGE UNIVERSITET (NMBU), As (NO); SYKEHUSET OSTFOLD HF, Gralum (NO); UNIVERSITY OF COPENHAGEN, Copenhagen (DK)

( * ) Notice: Subject to any disclaimer, the term of this patent is extended or adjusted under 35 U.S.C. 154(b) by 0 days.

(21) Appl. No.: 16/635,428

(22) PCT Filed: Aug. 2, 2018

(86) PCT No.: PCT/EP2018/071076
§ 371 (c)(1),
(2) Date: Jan. 30, 2020

(87) PCT Pub. No.: WO2019/025573
PCT Pub. Date: Feb. 7, 2019

(65) Prior Publication Data
US 2020/0368292 A1 Nov. 26, 2020

(30) Foreign Application Priority Data
Aug. 2, 2017 (GB) .................... 1712459

(51) Int. Cl.
*A61K 35/74* (2015.01)
*A61P 1/00* (2006.01)

(52) U.S. Cl.
CPC ............... *A61K 35/74* (2013.01); *A61P 1/00* (2018.01)

(58) Field of Classification Search
None
See application file for complete search history.

(56) References Cited

FOREIGN PATENT DOCUMENTS

| DK | 140492 A | 5/1994 |
|----|----------|--------|
| DK | 170824 B1 | 5/1994 |
| EP | 0306466 A2 | 3/1989 |
| EP | 0418187 B1 | 12/1994 |
| WO | 8908448 A1 | 9/1989 |
| WO | 9851693 A1 | 11/1998 |
| WO | 200068002 A1 | 11/2000 |
| WO | 0153525 | 7/2001 |
| WO | 200160974 A2 | 8/2001 |
| WO | 200207741 A1 | 1/2002 |
| WO | 2003068002 A1 | 8/2003 |
| WO | 2003068003 A1 | 8/2003 |
| WO | 03072133 A2 | 9/2003 |
| WO | 2005002606 A1 | 1/2005 |
| WO | 2010128312 A2 | 11/2010 |
| WO | 2011043654 A1 | 4/2011 |
| WO | 2012080754 A2 | 6/2012 |
| WO | 2014088982 A1 | 6/2014 |
| WO | 2016156251 A1 | 10/2016 |

OTHER PUBLICATIONS

Romarheim et al (J. Nutr. 141:124-130, 2011).*
GB 1712459.5 Search Report, dated Apr. 23, 2018, Sate of Search Apr. 20, 2018; 6 pages.
Indrelid et al.; "Computational and Experimental Analysis of the Secretome of Methylococcus Capsulatus"; PLoS ONE; 9(12): e114476; 18 pages (2014).
International Search Report and Written Opinion; International Appplication No. PCT/EP2018/071076; International Filing Date Aug. 2, 2018; dated Oct. 4, 2018; 16 pages.
Kleiveland et al.; "The Noncommensal Bacterium *Methylococcus capsulatus* (Bath) Ameliorates Dextran Sulfate (Sodium Salt)-Induced Ulcerative Colitis by Influencing Mechanisms Essential for Maintenance of the Colonic Barrier Function"; Applied and Environmental Microbiology; 79(1) pp. 48-56; (2013).
Al-Khedairy, E.; "In vitro release study on capsules and tablets containing enteric-coated granules prepared by wet granulation"; Iraqi Journal of Pharmceutical Sciences, vol. 15, Issue No. 1: 2006: 4 pages.

(Continued)

*Primary Examiner* — Brian Gangle
(74) *Attorney, Agent, or Firm* — Cantor Colburn LLP

(57) ABSTRACT

The invention provides a method for the treatment or prevention of GI tract dysbiosis in a subject, said method comprising administering an effective amount of a non-viable *Methylococcus capsulatus* or a lysate of *Methylococcus capsulatus* to said subject. The invention further provides a method for the treatment or prevention of a disease or condition selected from small intestine bacterial overgrowth (SIBO), small intestine fungal overgrowth syndrome (SIFO), GI tract cancers, breast cancer, neurological disorders, malnutrition, chronic fatigue syndrome, autism, cardiovascular diseases and GI tract infections in a subject with GI tract dysbiosis, said method comprising administering an effective amount of a non-viable *Methylococcus capsulatus* or a lysate of *Methylococcus capsulatus* to said subject. A non-viable *Methylococcus capsulatus* or a lysate of *Methylococcus capsulatus* for use in said methods is further provided.

8 Claims, 12 Drawing Sheets

(56) References Cited

OTHER PUBLICATIONS

Figure 1:
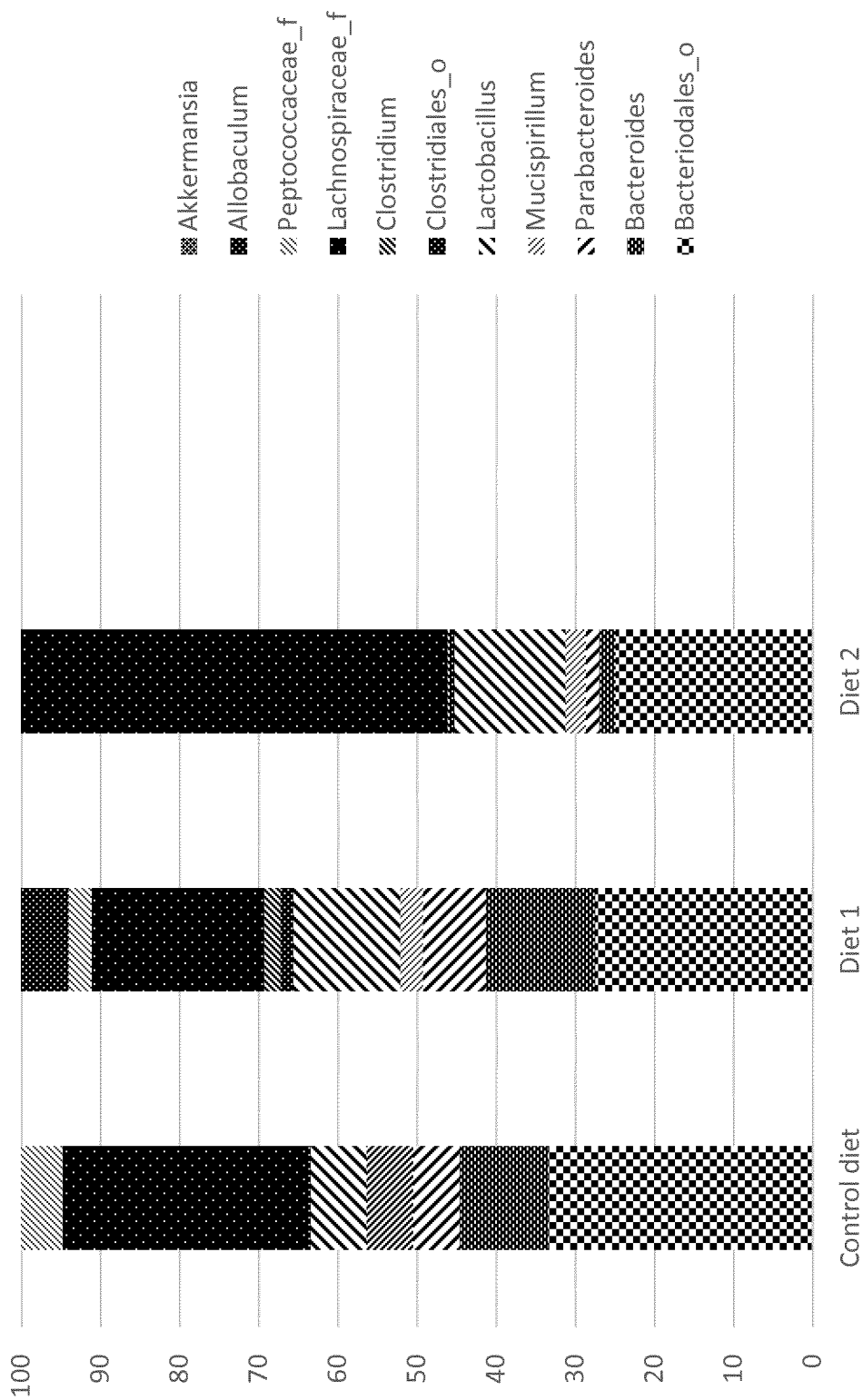

Casen, C. et al.,; "Deviations in human gut microbiota: a novel diagnostic test for determining dysbiosis in patients with IBS or IBD"; Alimentary Pharmacology and Therapeutics, vol. 42, Issue No. 1; 2015; pp. 71-83.

Christoffersen, T. e. et al.; "Effects of the non-commensal Methylococcus capsulatus Bath on mammalian immune cells"; Molecular immunology, vol. 66, Issue No. 2; 2015; pp. 107-116.

De Palma, G. et al.; "Transplantation of Fecal Microbiota From Patients With Irritable Bowel Syndrome Alters Gut Function and Behavior in Recipient Mice"; Science Translational Medicine, vol. 9, issue No. 379; 2017: eaaf6397. doi: 10.1126/scitranslmed. aaf6397; 14 pages.

Flint, H. et al.; "The role of the gut microbiota in nutrition and health"; Nature Reviews. Gastroenterology & Hepatology, vol. 9, Issue No. 10; 2012; pp. 577-589.

Jensen, B.; "Methylococcus capsulatus (Bath) Reverts Metabolic-Syndrome and Obesity-Associated Colitis"; a Poster presented by the University of Copenhagen Faculty of Science on Jul. 26, 2015.

Kleppe, G.: "Bioprotein, a new high quality single cell protein based on natural gas"; British Journal of Nutrition. vol. 90, issue No. 1; 2003; pp. 169-178.

Park, J. et al.; "Short-chain Fatty Acids Induce Both Effector and Regulatory T Cells by Suppression of Histone Deacetylases and Regulation of the mTOR-S6K Pathway"; Mucosal Immunology, vol. 8, issue No. 1; 2015; pp. 80-93.

Wang, X. et al.; "Interleukin-22 alleviates metabolic disorders and restores mucosai immunity in diabetes"; Nature, vol. 514, Issue No. 7521; 2014; pp. 237-241.

\* cited by examiner

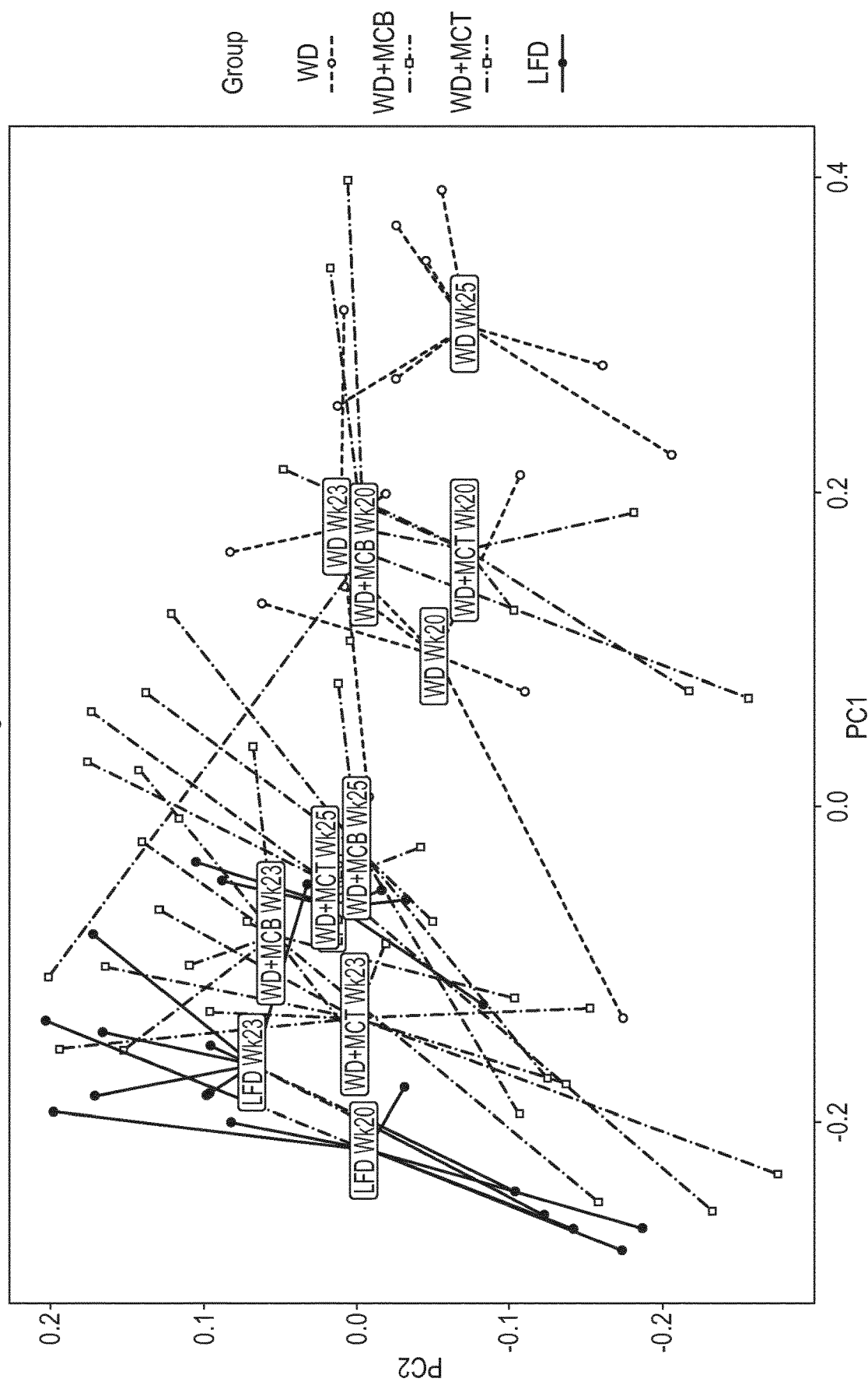

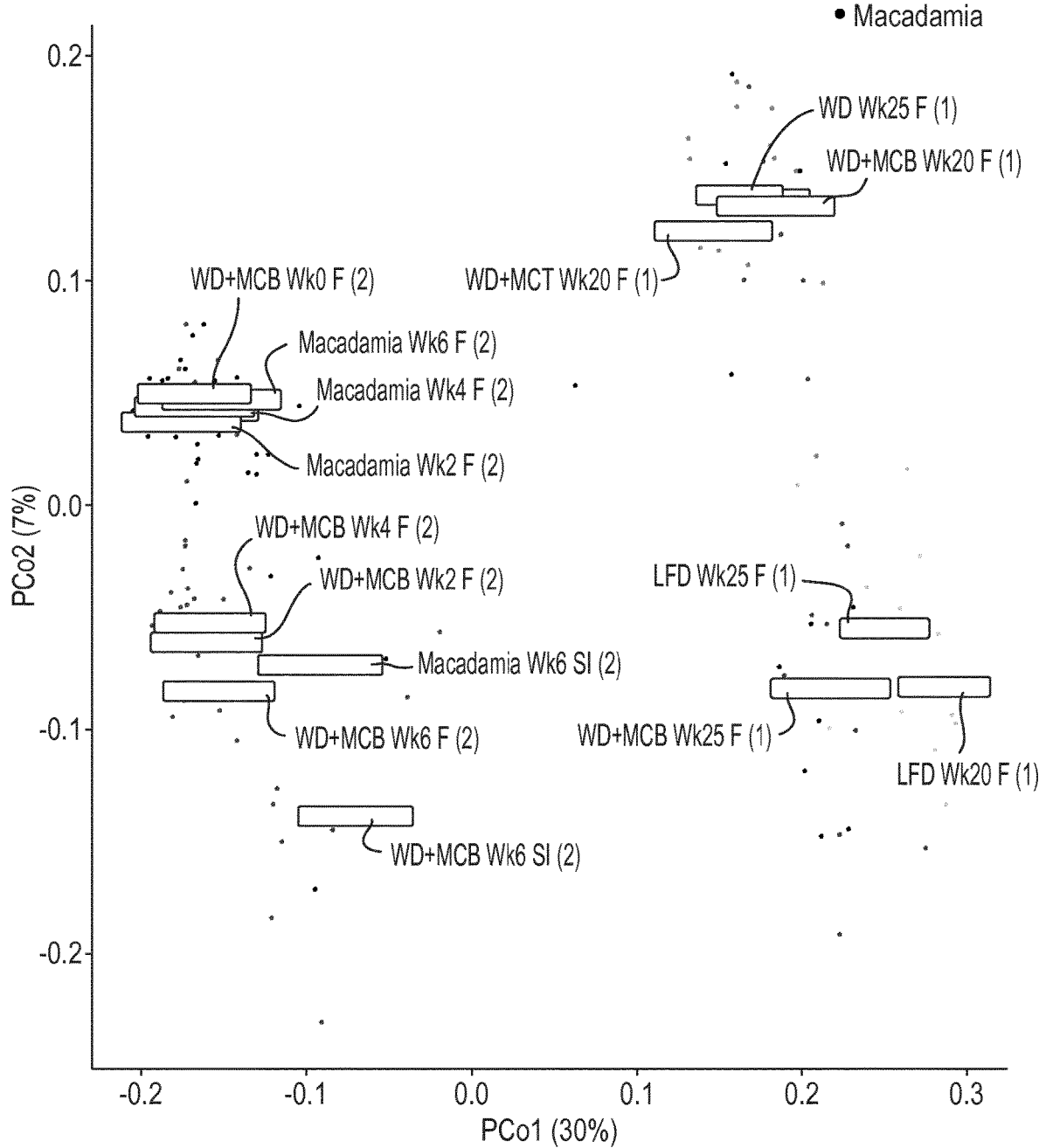

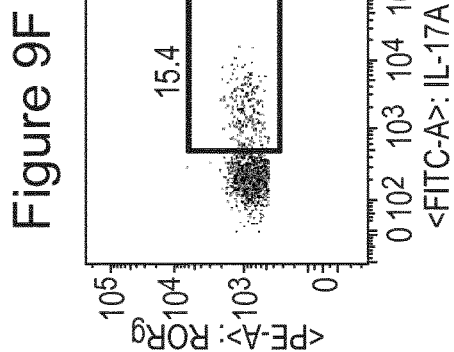
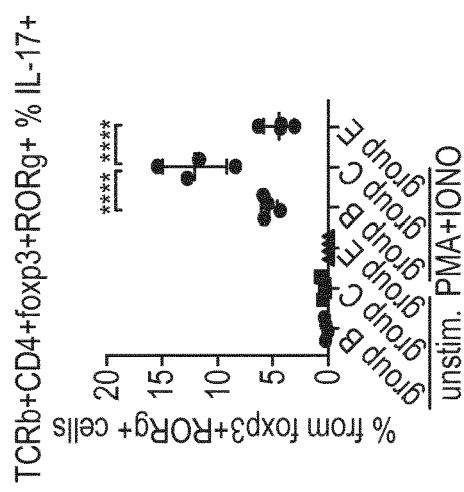
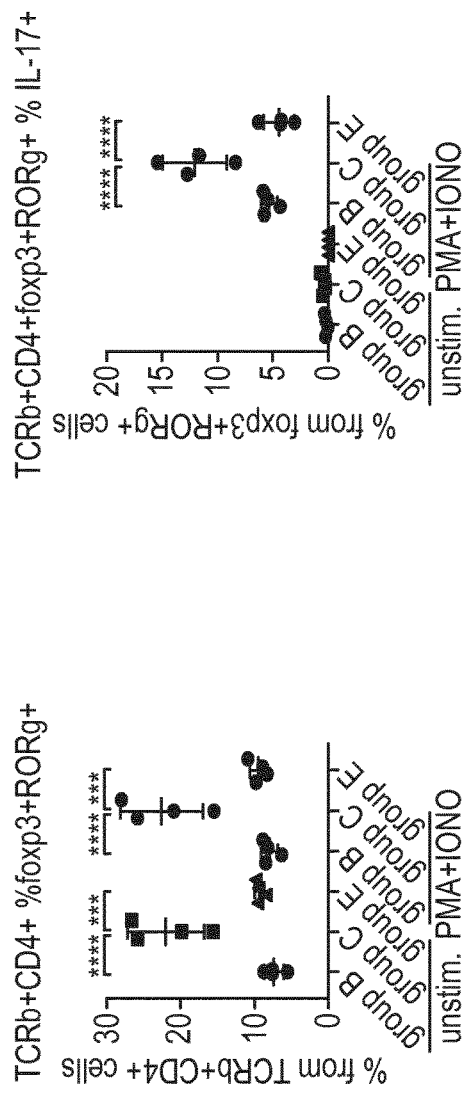
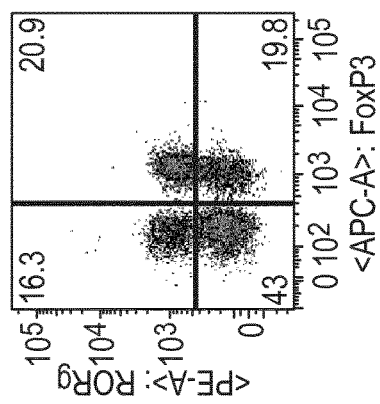
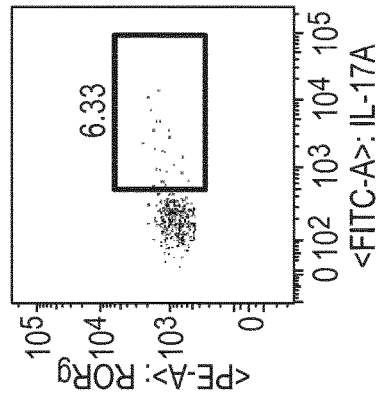
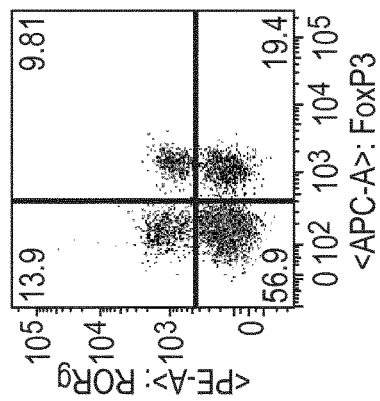

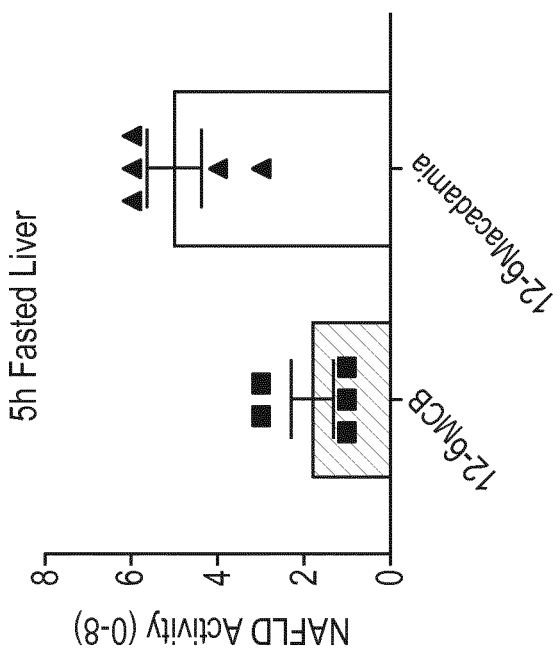
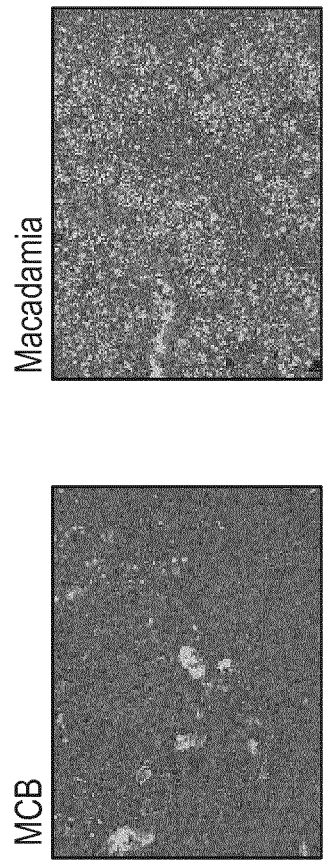

TREATMENT OR PREVENTION OF GASTROINTESTINAL DYSBIOSIS

CROSS REFERENCE TO RELATED APPLICATIONS

This application is a National Stage Application of PCT/EP2018/071076, filed on Aug. 2, 2018, which claims the benefit of GB Application No. 1712459.5, filed on Aug. 2, 2017, both of which are incorporated by reference in their entirety herein.

The present invention relates to the treatment or prevention of dysbiosis in the gastrointestinal (GI) tract of a subject. GI tract dysbiosis is a physiological state in which the microbiota profile of the GI tract of a subject, or part thereof, has diverged from a normal state. This divergence in GI tract microbiota profile has been observed to manifest in mild effects such as a reduction in the general health of a subject, but also in specific pathological diseases and conditions. More particularly, the invention relates to the use of a particular species of non-commensal, non-pathogenic methanotrophic soil bacterium, *Methylococcus capsulatus*, to normalise the microbiota profile in the GI tract of a subject with GI tract dysbiosis, or to maintain a normal GI tract microbiota profile in a healthy subject. By normalising the GI tract microbiota profile and/or maintaining a normal GI tract microbiota profile *Methylococcus capsulatus* can therefore reverse, mitigate and/or prevent the deleterious effects of GI tract dysbiosis on the health of a subject.

The GI tract of an animal, also referred to as the digestive tract or alimentary canal (and which terms may be used interchangeably with GI tract), is the continuous series of organs beginning at the mouth and ending at the anus. Throughout its length the GI tract is colonised by microorganisms of a variety of different species. Some 10-100 trillion microbes colonise the human gastrointestinal tract, with the highest numbers present in the colon. The physiology of these microbes and their hosts is closely connected and mutually regulated. The host shapes the composition of the intestinal microbiota at species and community levels by supplying nutrients and by producing antimicrobial peptides. The microbiota in return adds to the metabolic and biochemical activities of the host and plays essential roles, inter alia, in the development and differentiation of the host intestinal epithelium, the immune system and in the maintenance of mucosal homeostasis.

The total microorganism content of the GI tract is the microbiota of the GI tract. The identity and relative amounts of the constituent microorganisms or groups thereof can be considered to be a profile of the microbiota. Microbiota profiles therefore give information on microbial diversity (i.e. the number of taxonomically distinct microbes or distinct taxonomic groups which are present) in the GI tract as well as providing information on the relative amounts of the microbes or groups thereof which are present.

Many diseases and conditions, or stages thereof, are believed to be associated with perturbations in the microbiota of the GI tract, or regions thereof. In some instances the disease or condition may be caused by, or is exacerbated by, the shift in the profile of the microbiota of the GI tract, or regions thereof (i.e. the relative amounts of constituent microbes and the diversity of those microbes). Such deviations from the normal state (normobiosis) may be considered as dysbiosis (a dysbiotic state). The precise mechanism behind this causation is not well understood. It is clear that perturbation of the microbiota of the GI tract results in the underpopulation of certain microbes and/or the overpopulation of others and/or reductions in diversity and this causes a shift, or imbalance, in the relative activities of each microbe population. It is believed that this shift in microbial activities may cause a reduction in beneficial effects (e.g. synthesis of vitamins, short-chain fatty acids and polyamines, nutrient absorption, inhibition of pathogens, metabolism of plant compounds) to occur and/or an increase in deleterious effects (secretion of endotoxins and other toxic products) to occur with consequent overall negative effects on the host's overall physiology. These effects can then manifest as illness and disease.

Many diseases and conditions affecting the GI tract are associated with, e.g. exacerbated by, the development of microbiota profiles that deviate from the normal state. Such diseases include Inflammatory Bowel Disease (IBD), Crohn's Disease (CD), Ulcerative Colitis (UC), Irritable Bowel Syndrome (IBS), small bowel bacterial overgrowth syndrome and GI tract cancers (e.g. cancer of the mouth, pharynx, oesophagus, stomach, duodenum, jejunum, ileum, cecum, colon, rectum or anus). Evidence also exists of links between GI tract microbiota profiles and diseases and conditions that were previously considered to be, at best, distantly related to the GI tract; for instance breast cancer; ankylosing spondylitis; non-alcoholic steatohepatitis; the atopic diseases, e.g. eczema, asthma, atopic dermatitis, allergic conjunctivitis, allergic rhinitis and food allergies; metabolic disorders, e.g. diabetes mellitus (type 1 and type 2), obesity and metabolic syndrome; neurological disorders, e.g. multiple sclerosis, dementia, and Alzheimer's disease; psychiatric disorders, e.g. depression and anxiety; autoimmune disease (e.g. arthritis); malnutrition; chronic fatigue syndrome; autism; cardiovascular diseases (e.g. atherosclerosis, coronary heart disease (angina, myocardial infarction, heart failure, stroke, peripheral arterial disease); and GI tract infections (e.g. viral (e.g. rotavirus, norovirus, adenovirus, astrovirus), bacterial (e.g. *Escherichia, Helicobacter, Salmonella, Shigella, Clostridium, Staphylococcos,* and *Campylobacter*), parasitic (e.g. *Giardia, Entamoeba, Cryptosporidium, Trichuris*) and fungal). It is believed that perturbations of the GI tract microbiota profile (in terms of relative amounts and/or diversity), which may be considered to equate to an imbalance in the GI tract microbiota, contribute to these diseases, either by causing the diseases or contributing to their progression. It is also believed that many more diseases will be found to have causal links to perturbations of the GI tract microbiota profile.

Thus, treatments which can normalise a dysbiotic state in the GI tract of a subject or which can maintain a normal profile of microbiota in the GI tract of a subject continue to be sought.

It has now been found that lysates and other non-viable forms of *Methylococcus capsulatus* (Bath) (NCIMB 11132 now NCIMB 41526), a non-commensal, non-pathogenic, methanotrophic soil bacterium may be orally administered to animals with diet-induced GI tract dysbiosis and a normalisation of the GI tract microbiota profile was observed.

Thus, in a first aspect the invention provides a method for the treatment or prevention of GI tract dysbiosis in a subject, said method comprising administering an effective amount of a non-viable *Methylococcus capsulatus* or a lysate of *Methylococcus capsulatus* to said subject.

Expressed alternatively the invention provides a non-viable *Methylococcus capsulatus* or a lysate of *Methylococcus capsulatus* for use in the treatment or prevention of GI tract dysbiosis.

Thus, the invention also provides for the use of a non-viable *Methylococcus capsulatus* or a lysate of *Methylococ-*

*cus capsulatus* in the manufacture of a composition, e.g. a medicament, nutraceutical, food additive or foodstuff, for the treatment or prevention of GI tract dysbiosis.

As discussed previously, the treatment or prevention of GI tract dysbiosis may also be considered in terms of normalising a perturbed GI tract microbiota profile and maintaining a normal GI tract microbiota profile.

Thus, the invention may also be considered to provide a method for normalising a perturbed GI tract microbiota profile or maintaining a normal (healthy) GI tract microbiota profile in a subject, said method comprising administering an amount of a non-viable *Methylococcus capsulatus* or a lysate of *Methylococcus capsulatus* to said subject effective to normalise a perturbed GI tract microbiota profile of the subject or to maintain a normal (healthy) GI tract microbiota profile of the subject.

Expressed alternatively the invention provides a non-viable *Methylococcus capsulatus* or a lysate of *Methylococcus capsulatus* for use in normalising a perturbed GI tract microbiota profile or maintaining a normal GI tract microbiota profile.

Thus, the invention also provides for the use of a non-viable *Methylococcus capsulatus* or a lysate of *Methylococcus capsulatus* in the manufacture of a composition, e.g. a medicament, nutraceutical, food additive or foodstuff, for normalising a perturbed GI tract microbiota profile or maintaining a normal GI tract microbiota profile.

The GI tract is colonised by a plethora of microorganisms from a wide variety of taxonomic groups. The relative levels of those microorganisms or groups of microorganisms in the GI tract of a subject form the microbiota profile of the GI tract. It is important to note that such relative levels also provide information on the presence or absence of particular microorganisms or groups of microorganisms and therefore the diversity of the microbiota in any particular location or sample. In practical terms a GI tract microbiota profile is considered to be a representation, e.g. numerical or graphical, of the relative levels of a plurality of microorganisms or groups of microorganisms, more particularly a selection of microorganisms or groups of microorganisms from the GI tract that have been targeted for analysis. Thus, more usually it is a representation of the relative levels of a selected plurality of microorganisms or groups of microorganisms in a GI tract sample from a subject. The individual values for such levels (the individual profile elements) may be qualitative, quantitative or semi-quantitative, preferably quantitative. The term "amounts" could be used in place of "levels" if appropriate. A microbiota profile may additionally provide information of the metabolic phenotype of the microorganisms or groups of microorganisms in the GI tract of a subject, e.g. as measured at the level of the proteome, the transcriptome and/or the metabolome.

Dysbiosis is defined herein as a physiological state in which a subject displays (carries) a microbiota profile that differs or deviates significantly from a corresponding microbiota profile that is typical of a normal (healthy) subject, which may, in contrast, be referred to herein as "normobiosis" or a "normobiotic state". Dysbiosis may be also defined in terms of the extent of the perturbation in the relative levels, or the metabolic phenotype, of the microorganisms or groups of microorganisms contributing to the profile, i.e. by a measure of how different a microbiota profile is from a normal microbiota profile (normobiosis) or by how much a microbiota profile deviates from a normal microbiota profile. In the context of the present invention this terminology may be used interchangeably. In the more specific context of subjects with diseases and conditions associated with perturbations in the microbiota of the GI tract, dysbiosis may be more specifically defined as a microbiota profile that differs from the microbiota profile that is typical of a subject which does not have said disease or condition or is not at risk of developing said disease or condition.

The profiling of GI tract microbiota (i.e. the preparation of a GI tract microbiota profile) may involve any convenient means by which the levels of microorganisms or groups of microorganisms in the GI tract of a subject may be measured, preferably quantified. The profiling methods of use in accordance the invention are typically in vitro methods performed using any sample taken from the GI tract.

The gastrointestinal (GI) tract of vertebrates, also referred to as the digestive tract or alimentary canal, is the continuous series of organs beginning at the mouth and ending at the anus. Specifically, this sequence consists of the mouth, the pharynx, the oesophagus, the stomach (or stomachs in ruminant mammals), the duodenum, the small intestine, the large intestine and the anus. For the purposes of this invention, these organs can be subdivided into the upper GI tract, consisting of the mouth, pharynx, oesophagus, and stomach (s), and the lower GI tract (the intestinal tract), consisting of the duodenum, the jejunum, the ileum (together the small intestine), the cecum/appendix, the colon, the rectum (together the large intestine) and the anus.

A GI tract sample of use in the analysis of microbiota profiles in accordance the invention may include, but is not limited to, any fluid or solid taken from the lumen or surface of the GI tract or any sample of any of the tissues that form the organs of the GI tract. Thus the sample may be any luminal content of the GI tract, particularly the intestinal tract, (e.g. stomach contents, intestinal contents, caecal contents, mucus and faeces/stool, or combinations thereof) as well as samples obtained mechanically from the GI tract e.g. by swab, rinse, aspirate or scrape of a GI tract cavity or surface or by biopsy of a GI tract tissue/organ. Faecal samples are preferred. Faecal samples may be collected by the swab, rinse, aspirate or scrape of the rectum or anus or, most simply, the collection of faeces during or after defecation.

The sample may be used in accordance with the invention in the form in which it was initially retrieved. The sample may also have undergone some degree of manipulation, refinement or purification before being used in the methods of the invention. Thus the term "sample" also includes preparations thereof, e.g. relatively pure or partially purified starting materials, such as semi-pure preparations of the above-mentioned samples. Further included is the product of the microbial culture of said sample.

The purification may be slight, for instance amounting to no more than the concentration of the solids, or cells, of the sample into a smaller volume or the separation of cells from some or all of the remainder of the sample.

In certain embodiments a preparation of the nucleic acid from the above mentioned samples, preferably a preparation in which the nucleic acids have been labelled, is used as the sample in accordance with the invention. Such preparations include reverse transcription products and/or amplification products of such samples or nucleic acid preparations thereof. In other embodiments nucleic acids may be prepared for analysis by means which do not involve PCR e.g. Loop Mediated Isothermal Amplification (LAMP), Nucleic Acid Sequence Based Amplification (NASBA or 3SR), Strand Displacement Amplification (SDA), Rolling Circle Amplification (RCA), Ligase Chain Reaction (LCR), Helicase dependant amplification (HAD), Ramification amplification method (RAM), MALBAC (Multiple Annealing and Looping Based Amplification Cycles) and MDA (Multiple Displacement Amplification), or means which do not involve amplification at all, e.g. the TruSeq DNA PCR-Free system of Illumina and the Hyper Prep system of KAPA and the NxSeq AmpFREE Low DNA Library system of Lucigen.

It may be advantageous if the predominant nucleic acid of the nucleic acid preparation is DNA, however, RNA may be the predominant nucleic acid in other embodiments. These preparations include relatively pure or partially purified nucleic acid preparations.

Techniques for the isolation of nucleic acid from samples, including complex samples, are numerous and well known in the art and described at length in the literature. The techniques described in WO98/51693 and WO01/53525 can be employed to prepare nucleic acids from the above-mentioned samples.

Unless context dictates otherwise, the term "corresponding sample" is used herein to refer to samples of the same type which have been obtained from different subjects and/or at different times in essentially the same way and to which any substantive processing or handling thereof has taken place in essentially the same way.

Methods for measuring the relative levels of GI tract microbiota in a sample include but are not limited to nucleic acid analysis (e.g. nucleic acid sequencing approaches, oligonucleotide hybridisation probe based approaches, primer based nucleic acid amplification approaches), antibody or other specific affinity ligand based approaches, proteomic and metabolomic approaches.

The analysis of ribosomal RNA genes and the transcripts thereof, e.g. the 5S, 16S and 23S genes (preferably the 16S gene) in prokaryotic microorganisms or the 18S gene in eukaryotic microorganisms, may be convenient.

Preferably, the analysis of the sample will be by nucleic acid sequence analysis and may take the form of a sequencing technique, e.g. the Sanger dideoxynucleotide sequencing method or a so-called "next generation" or "second generation" sequencing approaches (in reference to the Sanger dideoxynucleotide method as the "first generation" approach) including those utilising pyrosequencing, reversible terminator sequencing, cleavable probe sequencing by ligation, non-cleavable probe sequencing by ligation, DNA nanoballs, and real-time single molecule sequencing. RNA sequencing (e.g. in the context of transcriptome analysis) may be used in other embodiments.

Nucleic acid sequence analysis may also preferably take the form of an oligonucleotide hybridisation probe based approach in which the presence of a target nucleotide sequence is confirmed by detecting a specific hybridisation event between a probe and its target. In these approaches the oligonucleotide probe is often provided as part of a wider array, e.g. an immobilised nucleic acid microarray. Preferably, the oligonucleotide probe sets and associated methods of WO 2012/080754 and WO 2011/043654 may be used to prepare microbiota profiles in accordance with the present invention.

A typical microbiota profile of a normal (healthy) subject may be obtained from a single subject or even a single sample from a single subject, but preferably will be obtained from a plurality of subjects and the techniques used will allow for intra-individual variation. Preferably the samples and physical means (including the sample collection and handling procedures and the test procedures performed on the sample) used to prepare the microbiota profiles from normal subjects and the test subject are essentially the same in order to permit direct comparison of the results so obtained.

Comparison between the profile from a test sample and that of a normal (healthy) reference in order to assess whether the test sample is dysbiotic (or normobiotic) and, optionally, the extent of any dysbiosis may be achieved by any convenient means and the choice of approach used may be dictated by the form of the data making up the profiles under comparison. Depending on the nature of the data, the comparison may be a qualitative, semi-quantitative or quantitative process.

In the context of the present invention, for a microbiota profile from a test sample to correspond to that of a microbiota profile from a normal subject (i.e. to be considered normobiotic) is to be substantially, e.g. essentially, the same as (or to be similar to, or equivalent to, or to match or to fit) the normal (healthy) reference profile. In certain embodiments it may be determined whether or not the profiles are statistically similar or statistically equivalent.

Thus, it will be seen that the comparison of the test and reference profiles and determining whether or not they correspond may be performed using mathematical or statistical techniques. Generally this will be implemented by software (i.e. such analyses will be performed using a computer). Statistical or mathematical methods for performing such a comparison and determination of correspondence are well known and widely available in the art. In certain embodiments, it may be determined whether the test profile is statistically more similar to a healthy profile than not in order to classify, or identify, the patient as having a normal microbiota profile (normobiosis) and thus is not dysbiotic (does not have dysbiosis). Suitable statistical analyses may include, data clustering analysis, ordination, Bayesian statistics, Fisher statistics, correlation analysis, probability analysis, dimensionally reduction analysis and machine learning. As examples this includes, but is not limited to, principal component analysis, principal coordinate analysis, non-parametric multidimensional scaling, analysis of variance using distance matrices, similarity and dissimilarity measures, permutational multivariate analysis of variance, analysis of variance using absolute, normalised or relative values, Students t-test, Mantel test and Kruskal-Wallis test.

In other embodiments GI tract dysbiosis is considered to be present if the microbiota diversity in a GI tract sample is significantly different to that of a sample from a normal (healthy) subject. Microbiota diversity may be measured with statistical techniques for species (used in this context in its mathematical rather than taxonomic sense) diversity in a population. An example of such a technique is the Shannon Index. Further examples include those mentioned immediately above.

Conveniently, the dysbiosis status of a GI tract sample from a test subject may be assessed using the Dysbiosis Index test described in Casén, C., et al, 2015, Aliment Pharmacol Ther., 42(1):71-83 and WO 2016/156251. This test can analyse GI tract microbiota profiles from test samples in comparison to those from healthy subjects and apply a relative score proportional to the extent of dysbiosis in the sample. Thus a sample may be classified as being dysbiotic or not and the extent of any dysbiosis may also be determined. Changes in the dysbiotic/normobiotic status of a subject can therefore be easily monitored before, during and/or after treatment.

Alternatively or additionally a subject may be considered dysbiotic if their GI tract microbiota profile corresponds to, i.e. is substantially, e.g. essentially, the same as (or is similar to, or equivalent to, or matches or fits) that of a subject or group of subjects which are considered to be dysbiotic. This may be convenient if a particular dysbiotic profile (e.g. those described below) is of interest. The above discussion of the preparation and comparison of normobiotic profiles applies mutatis mutandis to the preparation and comparison of dysbiotic profiles.

As shown in the Examples, an orally administered lysate of *Methylococcus capsulatus* (Bath) is able to normalise faecal microbiota profiles including the levels of certain specific microorganisms or groups of microorganisms. The methods of the invention are therefore directed to the use of lysates and non-viable forms of *Methylococcus capsulatus* to combat dysbiosis and promote normobiosis in the GI tract of vertebrate animals, particularly humans and non-human mammals, birds and fish.

Thus, in accordance with the invention lysates and non-viable forms of *Methylococcus capsulatus* may be used to normalise the GI tract microbiota of a subject which has dysbiosis in at least a part of their GI tract. In other words, lysates and non-viable forms of *Methylococcus capsulatus* may be used to treat dysbiosis. The terms "treatment", "normalisation" and "to normalise" in these contexts encompasses any positive effect on the dysbiosis (the abnormal microbiota profile) of the subject. As such not only is complete normalisation of the microbiota profile covered (i.e. a return to normobiosis or a "normalised" or normal microbiota profile) but partial improvement in the dysbiosis of the subject. Improvement may be partial in the sense that perturbations in the levels of, or the metabolic phenotypes of, a subset of the microorganisms or groups of microorganisms in the profile are improved (preferably normalised) and/or that the extent of perturbation in the levels of, or the metabolic phenotypes of, particular microorganisms or groups of microorganisms is partially reduced. Preferably the GI tract microbiota of a subject which has dysbiosis is (fully) normalised.

It will be seen that the perturbations in the levels of, or the metabolic phenotypes of, microorganisms or groups of microorganisms which give rise to a finding of dysbiosis include those which result in levels of, or the metabolic phenotypes of, particular microorganisms or groups of microorganisms which are greater than normal, as well as levels of, or the metabolic phenotypes of, particular microorganisms or groups of microorganisms which are less than normal. In the extreme, this may be seen as the absence of a particular microorganism or group of microorganisms (reduction in microbiota diversity) or in the abnormal presence of a particular microorganism or group of microorganisms. Different regions of the GI tract may have different parameters for what constitutes normal and so the presence or absence of a particular microorganism or group of microorganisms in one part of the GI tract may be normal elsewhere in the GI tract.

In accordance with the invention the term "normalisation" encompasses any change which brings any levels of, or the metabolic phenotypes of, microorganisms or groups of microorganisms which are considered abnormal for a sample or region of the GI tract in question back towards a normal state. Thus, normalisation includes both an increase in (the enrichment of) a particular microorganism or groups of microorganism or metabolic phenotypes thereof which was underpopulated in the sample or region of the GI tract in question and/or a reduction in (the elimination of) a particular microorganism or group of microorganisms or metabolic phenotypes thereof which was overpopulated in the sample or region of the GI tract in question. This may include a normalisation in the diversity of the microbiota in the sample or region of the GI tract in question.

Also in accordance with the invention lysates and non-viable forms of *Methylococcus capsulatus* may be used to maintain a normal microbiota profile (normobiosis) in the GI tract of a subject or part thereof. In these contexts, the term "maintain" encompasses the substantially continuous persistence of a normal microbiota profile in the GI tract of a subject, or part thereof, during a period of administration of effective amounts of lysates and non-viable forms of *Methylococcus capsulatus*. In these embodiments, significant perturbation in the levels of, or the metabolic phenotypes of, one or more microorganisms or groups of microorganisms does not occur. Thus, lysates and non-viable forms of *Methylococcus capsulatus* may be used to prevent dysbiosis in a subject. In these contexts, the term "prevention" refers to any prophylactic or preventative effect against dysbiosis. It thus includes limiting, reducing or preventing dysbiosis or the extent thereof (more specifically perturbation in the levels of, or the metabolic phenotypes of, one or more microorganisms or groups of microorganisms in the GI tract of the subject or part thereof) and also delaying, limiting, reducing or preventing the onset of the dysbiosis relative to the status of the subject prior to the prophylactic treatment. Prophylaxis thus explicitly includes both absolute prevention of occurrence or development of dysbiosis, any delay in the onset or development of dysbiosis, and/or any reduction or limitation on the extent of dysbiosis.

In embodiments in which the Dysbiosis Index described in Casén, C., et al, supra is used to measure dysbiosis in a subject, treatment of a subject in accordance with the invention may change the DI score towards the normobiosis end of the scoring range and away from the dysbiosis end of the range (indicative of the treatment of dysbiosis and a normalising of the microbiota in that subject) or a least maintain the DI score (indicative that further increase in dysbiosis has been prevented or normobiosis has been maintained).

It may be found that in the context of differing pathologies and even within different stages and severities of a particular pathology, subjects may display different patterns of dysbiosis in their GI tract microbiota and/or the deleterious effects of dysbiosis is mediated by certain key microorganisms or groups of microorganisms.

Thus, in certain embodiments the methods of invention may treat or prevent perturbations in the levels of (i.e. dysbiosis in), or normalise or maintain normal levels of, particular microorganisms or groups of microorganisms in the GI tract of the subject.

The levels of *Actinobacteria* (e.g. *Atopobium, Bifidobacterium*); *Bacteroidetes* (e.g. *Bacteroidia*, e.g. *Bacteroidales*, e.g. *Alistipes, Bacteroides* (in particular *Bacteroides fragilis* and *Bacteroides vulgates*) *Parabacteroides, Prevotella* (in particular *Prevotella copri*)); *Firmicutes* (e.g. *Allobaculum, Bacilli*, e.g. *Bacillus, Lactobacillus, Pediococcus, Streptococcus; Clostridia*, e.g. *Anaerotruncus, Blautia, Clostridium, Desulfitispora, Dorea, Eubacterium, Faecalibacterium, Ruminococcus; Erysipelotrichia*, e.g. *Catenibacterium, Coprobacillus*, Unclassified *Erysipelotrichaceae; Negativicutes*, e.g. *Dialister, Megasphaera, Phascolarctobacterium* (in particular *Dialister invisus, Faecalibacterium prausnitzii, Ruminococcus albus, Ruminococcus bromii, Ruminococcus gnavus, Streptococcus sanguinis, Streptococcus thermophilus*)); *Proteobacteria* (e.g. *Epsilon proteobacteria*, e.g. *Veillonella/Helicobacter; Gamma proteobacteria*, e.g. *Acinetobacter, Pseudomonas, Salmonella, Citrobacter, Cronobacter, Enterobacter, Shigella, Escherichia*), *Teneri-* cutes (e.g. *Mollicutes*, e.g. *Mycoplasma* (in particular *Mycoplasma hominis*), *Verrucomicrobia* (e.g. *Verrucomicrobiae*, e.g. *Akkermansia* (in particular *Akkermansia munciniphila*)) and *Deferribacteres*, e.g. *Mucispirillum* (in particular *Mucispirillum schaedleri*) in the GI tract may be of particular importance and so in preferred embodiments the methods of the invention normalise or maintain normal levels (treat or prevent dysbiosis of (perturbations in)) one or more, e.g. at least 2, 3, 4, 5, 6, 7, 8, 9, 10 or all of the above microorganisms or groups of microorganisms.

In the context of certain human pathologies the levels of *Firmicutes* (*Bacilli* and *Faecalibacterium prausnitzii* in particular), *Proteobacteria* (*Shigella/Escherichia* in particular), *Bacteroidetes* (*Bacteroides* and *Prevotella*, *Bacteroides fragilis*, *Bacteroides vulgates* and *Prevotella copri* in particular), *Actinobacteria* and *Ruminococcus gnavus* in the GI tract may be of particular importance and so in preferred embodiments the methods of the invention normalise or maintain normal levels (treat or prevent dysbiosis of (perturbations in)) one or more, e.g. at least 2, 3, 4, 5 or all of these microorganisms or groups of microorganisms), preferably in a human subject.

In the context of certain rodent, e.g. murine, pathologies the levels of *Firmicutes*, *Proteobacteria*, *Bacteroidetes*, *Mucispirillum*, *Akkermansia* and *Allobaculum* in the GI tract may be of particular importance and the methods of the invention normalise or maintain normal levels (treat or prevent dysbiosis of (perturbations in)) one or more, e.g. at least 2, 3, 4 or all of these groups of microorganisms).

The above-described methodologies for determining dysbiosis in general terms may be adapted to analyse and compare the levels and/or the metabolic phenotypes of the microorganisms and groups of microorganisms of these embodiments specifically.

In these embodiments, if one microorganism or groups of microorganisms is particularised as essential to the method of the invention, references herein to at least 2, 3, etc. microorganisms or groups should be interpreted as being references to the particularised microorganism of group plus at least 1, 2, etc. of the remaining microorganisms or groups. The same interpretation should be applied to embodiments in which a plurality of microorganisms or groups are particularised.

Many diseases and conditions, or stages thereof, are believed to be associated with perturbations in the microbiota of the GI tract, or regions thereof, such diseases include, but are not limited to, inflammatory bowel disease (IBD) (e.g. Crohn's disease, ulcerative colitis (UC)), irritable bowel syndrome (IBD), small intestine bacterial overgrowth (SIBO) small intestine fungal overgrowth syndrome (SIFO), GI tract cancers (e.g. cancer of the mouth, pharynx, oesophagus, stomach, duodenum, jejunum, ileum, cecum, colon, rectum or anus), breast cancer, autoimmune disease (e.g. arthritis, ankylosing spondylitis, celiac disease), non-alcoholic steatohepatitis, the atopic diseases (e.g. eczema, asthma, atopic dermatitis, allergic conjunctivitis, allergic rhinitis and food allergies, metabolic disorders, (e.g. diabetes mellitus (type 1 and type 2), obesity and metabolic syndrome), neurological disorders (e.g. multiple sclerosis, dementia and Alzheimer's disease), psychiatric disorders (e.g. depression and anxiety), malnutrition, chronic fatigue syndrome, autism, cardiovascular diseases (e.g. atherosclerosis, coronary heart disease (angina, myocardial infarction, heart failure, stroke, peripheral arterial disease) and GI tract infections (e.g. viral (e.g. rotavirus, norovirus, adenovirus, astrovirus), bacterial (e.g. *Escherichia*, *Salmonella*, *Shigella*, *Clostridium*, *Staphylococcus*, and *Campylobacter*), parasitic (*Giardia*, *Entamoeba*, *Cryptosporidium* and *Trichuris*) and fungal).

Thus, in certain embodiments, the treatment or prevention of dysbiosis in accordance with the invention can lead to the treatment or prevention any one of the above mentioned diseases or conditions, in particular is small intestine bacterial overgrowth (SIBO) small intestine fungal overgrowth syndrome (SIFO), GI tract cancers (e.g. cancer of the mouth, pharynx, oesophagus, stomach, duodenum, jejunum, ileum, cecum, colon, rectum or anus), breast cancer, neurological disorders (e.g. multiple sclerosis, dementia and Alzheimer's disease), psychiatric disorders (e.g. depression and anxiety), malnutrition, chronic fatigue syndrome, autism, cardiovascular diseases (e.g. atherosclerosis, coronary heart disease (angina, myocardial infarction, heart failure, stroke, peripheral arterial disease) and GI tract infections (e.g. viral (e.g. rotavirus, norovirus, adenovirus, astrovirus), bacterial (e.g. *Escherichia*, *Helicobacter*, *Salmonella*, *Shigella*, *Clostridium*, *Staphylococcus*, and *Campylobacter*), parasitic (*Giardia*, *Entamoeba*, *Cryptosporidium* and *Trichuris*) and fungal).

In other embodiments the invention provides a method for the treatment or prevention of any one of the above mentioned diseases or conditions in a subject with GI tract dysbiosis, said method comprising administering an effective amount of a non-viable *Methylococcus capsulatus* or a lysate of *Methylococcus capsulatus* to said subject. An effective amount may be an amount which is effective to treat or prevent GI tract dysbiosis in the subject.

In more particular embodiments the target disease or condition is small intestine bacterial overgrowth (SIBO) small intestine fungal overgrowth syndrome (SIFO), GI tract cancers (e.g. cancer of the mouth, pharynx, oesophagus, stomach, duodenum, jejunum, ileum, cecum, colon, rectum or anus), breast cancer, neurological disorders (e.g. multiple sclerosis, dementia and Alzheimer's disease), psychiatric disorders (e.g. depression and anxiety), malnutrition, chronic fatigue syndrome, autism, and cardiovascular diseases (e.g. atherosclerosis, coronary heart disease (angina, myocardial infarction, heart failure, stroke, peripheral arterial disease).

The invention further provides a non-viable *Methylococcus capsulatus* or a lysate of *Methylococcus capsulatus* for use in such methods and the use of a non-viable *Methylococcus capsulatus* or a lysate of *Methylococcus capsulatus* in the manufacture of a composition, e.g. medicament, nutraceutical, food additive or foodstuff, for use in such methods.

In certain embodiments the methods of the invention may further comprise a preceding step in which it is determined whether or not the subject has dysbiosis in at least part of their GI tract or is at risk of developing dysbiosis in at least part of their GI tract. In other embodiments the severity (extent) of dysbiosis may be determined. This may be by using the methodologies described above, e.g. those described in Casén, C., et al, supra, and WO 2016/156251. In the more specific embodiments of said method said preceding step may determine whether or not the subject has perturbations in the particular microorganisms or groups of microorganisms described above, as appropriate to the context in question. In other embodiments the severity (extent) of such perturbations may be determined.

In certain embodiments the methods of the invention may further comprise a preceding step in which it is determined whether or not the subject has, or is at risk of developing, one or more of the above mentioned target disease or condition. This step may be in addition to another preceding step in which it is determined whether or not the subject has dysbiosis in at least part of their GI tract or is at risk of developing dysbiosis in at least part of their GI tract, but the step of assessing dysbiosis of the risk thereof is not essential.

In other embodiments the methods of the invention may further comprise a following step in which it is determined whether or not the subject has dysbiosis in at least part of their GI tract or is at risk of developing dysbiosis in at least part of their GI tract. In other embodiments the severity (extent) of dysbiosis may be determined. In the more specific embodiments of said method said following step may determine whether or not the subject has perturbations in the particular microorganisms or groups of microorganisms described above, as appropriate to the context in question. In other embodiments the severity (extent) of such perturbations may be determined. The results of the analysis performed in the following step may be compared to a corresponding assessment made prior to, or earlier in, said treatment in order to determine any changes therein. Thus, inter alia, the status of the subject's dysbiosis may be monitored for any improvement or slowing of worsening following treatment or the on-going prevention of normobiosis may be confirmed.

In other embodiments the methods of the invention may further comprise a following step in which in which it is determined whether or not the subject has, or is at risk of developing, one or more of the above mentioned target disease or condition. This step may be in addition to another following step in which it is determined whether or not the subject has dysbiosis in at least part of their GI tract or is at risk of developing dysbiosis in at least part of their GI tract, but the step of assessing dysbiosis of the risk thereof is not essential. The results of the analysis performed in the following step may be compared to a corresponding assessment made prior to, or earlier in, said treatment in order to determine any changes in the target disease or condition. Thus, inter alia, the status of the subject's target disease or condition may be monitored for any improvement or slowing of worsening following treatment or the on-going prevention of said target disease or condition may be confirmed.

In accordance with the invention any strain of *M. capsulatus* may be used. In certain embodiments the strain may be selected from *M. capsulatus* Bath (e.g. that deposited as NCIMB 11132), *M. capsulatus* Texas (e.g. that deposited NCIMB 11853) and *M. capsulatus* Aberdeen, or mixtures of two or three thereof. In certain embodiments *M. capsulatus* Bath is used. In accordance with the invention references to a strain of *M. capsulatus* encompasses variants thereof which retain the essential characteristics of the reference strain in question and, in particular, the ability to combat dysbiosis as defined herein.

The selected *M. capsulatus* is used in the invention in a form which is substantially, e.g. essentially, incapable of colonising the subject to which it is administered. In certain embodiments this may be a substantially intact *M. capsulatus* cell which has been rendered non-viable (inactivated) and/or a lysate of an *M. capsulatus* cell (i.e. the remnants of a disrupted *M. capsulatus* cell). Typically, the selected *M. capsulatus* may be part of a culture, preferably a substantially pure culture, of *M. capsulatus* which has been rendered non-viable and/or be the lysate of a culture, preferably a substantially pure culture, of *M. capsulatus* (i.e. the remnants of a culture in which the individual *M. capsulatus* cells have been disrupted). In accordance with the invention the term "non-viable" is considered to mean a form of *M. capsulatus* which is substantially, e.g. essentially, incapable of colonising the subject to which it is administered. Lysates of *M. capsulatus* which may be used in the invention may therefore also be considered non-viable.

Colonisation may be considered to be the replication (growth in numbers) of *M. capsulatus* in the subject to which it has been administered. In other embodiments this may be measured in vitro by monitoring growth on any standard culture medium for the isolation of bacteria from clinical specimens, e.g. blood media, Luria Bertani media, tryptic soy media, nutrient media, under physiological conditions.

In other embodiments the *M. capsulatus* used in the invention is in a form which is not alive, i.e. is dead. A microorganism is considered to be alive if it can be induced to replicate and/or grow, or at least display morphological changes, when placed in a medium that would normally support the growth of that microorganism and/or the microorganism is metabolising nutrients to release energy to support cellular functions. Typically, a microorganism can be considered to be dead if cell membrane integrity is lost.

Thus, in certain embodiments the *M. capsulatus* used in the invention should show substantially, e.g. essentially, no growth on nitrate mineral salts medium (ATCC medium 1306) at 45° C. and pH 6.8 in an atmosphere of 75% air, 23.25% $CH_4$, and 1.25% $CO_2$. Growth of the *M. capsulatus* may be determined by appropriate standard means, e.g. by monitoring the size of the microorganism, the morphology of the microorganism, the number of microorganisms in the colony over time, the consumption of nutrients in the culture media, etc.

In other embodiments the *M. capsulatus* used in the invention should show substantially, e.g. essentially, no signs of metabolism. Monitoring levels of metabolism of *M. capsulatus* can be done routinely in a number of ways. For instance the levels of ATP can be measured. Only living cells with intact membranes can synthesis ATP and because ATP is not stored in cells, levels of ATP drop rapidly upon cell death. Monitoring ATP levels therefore gives an indication of the status of the *M. capsulatus*. A yet further option is to measure the reducing potential of the cell. Viable microorganisms metabolising nutrients use reducing reactions, by applying a marker that gives different outputs whether in reduced or oxidised form (e.g. a fluorescent dye) to the microorganism, the microorganism's reducing potential can be assessed. Microorganisms that lack the ability to reduce the marker can be considered to be dead. The MTT and MTS assays are convenient examples of this type of assay.

In other embodiments the *M. capsulatus* used in the invention should show substantial, e.g. complete, loss of cell membrane integrity. Membrane impermeable dyes (e.g. trypan blue and propidium iodide) are routinely used to assess membrane integrity. These dyes are excluded from intact microorganisms and so no staining occurs in such microorganisms. If cell membrane integrity is compromised, these dyes can access the microorganism and stain intracellular components. Alternatively, or in addition, dyes that only stain microorganisms with intact membranes are used to give an indication of the viability (or non-viability) of the cell. The Live/Dead Assay of Invitrogen Ltd is an assay that uses two dyes, one to stain dead cells, the other to stain live cells. Another approach to assessing membrane integrity is to detect the release of cellular components into the culture media, e.g. lactate dehydrogenase.

By "growth of a microorganism" it is meant both an increase in the size of the microorganism or in the amount and/or volume of the constituents of a microorganism (e.g. the amount of nucleic acid, the amount of protein, the number of nuclei, the numbers or size of organelles, the volume of cytoplasm) and an increase in the numbers of a microorganism i.e. an increase in the replication of a microorganism.

Typically growth of a microorganism is accompanied by the enlargement of the microorganism. The growth of a microorganism can be measured with routine techniques. For instance, microscopic examination of microorganism morphology over time, or assays to measure changes in the quantities of protein or nucleic acid (e.g. DNA) in general, or the changes in the quantities of specific proteins or nucleic acids, can be used. The skilled person would easily be able to select suitable markers to follow. Conveniently, so called housekeeping genes (e.g. GAPDH (glyceraldehyde 3-phosphate dehydrogenase), SDH (succinate dehydrogenase), HPRT1 (hypoxanthine phosphoribosyl transferase 1) and HBS1L (HBS1-like protein)), and 16S RNA genes and their expression products can be monitored.

By "replication of a microorganism" it is meant the act by which a microorganism reproduces. Typically this is by binary fission where a microorganism divides into two, but can also be by budding mechanisms where multiple progeny can arise from a microorganism. To support the division of the microorganism into two, binary fission is normally preceded by enlargement of the dividing microorganism and an increase in the amount and/or volume of cellular constituents Replication results in an increase in the number of cells/particles and so may be followed by any method of assessing microorganism numbers in a population. Another option is to follow the process in real time by visual examination with a microscope. The time it takes for a microorganism to replicate (i.e. produce another version of itself) is the generation time. Generation time will depend on the type of microorganism, its mode of replication and the conditions in which the microorganism is found. The rate of replication can be expressed in terms of the generation time.

*M. capsulatus* may be rendered non-viable (inactivated) by any convenient means, e.g. chemically (e.g. formaldehyde, hydrogen peroxide, guanidium thiocyanate, peracetic acid or cupric ascorbate), by irradiation (e.g. UV, X-ray, gamma ray, IR, microwave), or thermally (e.g. pasteurisation, freeze drying, lyophilisation) or by lysis (e.g. by mechanical means, hydrolysis and autolysis or combination thereof). Thus the *M. capsulatus* of use in the invention may specifically be a lysate of an *M. capsulatus* cell or a culture thereof.

Mechanical means for lysing *M. capsulatus* cells may include, but are not limited to impact based techniques (e.g. bead mills), shear stress based techniques (e.g. microfluidisers, rotor-stator homogenisers, the French pressure cell press), hydrostatic pressure based techniques, cryopulverisation, nitrogen decompression and ultrasonic homogenisation (sonication). Lysates prepared by shear stress based techniques, in particular a French pressure cell press, may be of note. Further lysis techniques are described in WO 01/60974, the contents of which are incorporated herein by reference.

WO 03/068002 and WO 03/068003 describe processes for preparing bacterial hydrolysates and autolysates, respectively, and their contents are incorporated herein in their entirety to the extent applicable to *M. capsulatus*.

*M. capsulatus* hydrolysates may therefore be produced by the action of one or more enzymes or chemicals capable of hydrolysing (e.g. hydrolytically degrading) *M. capsulatus* cell structure and/or intracellular components thereof. In certain embodiments this may be an enzyme or enzyme system capable of hydrolysing the protein and/or nucleic acid content of the *M. capsulatus* cells.

*M. capsulatus* autolysates may be prepared by incubation of *M. capsulatus* under carefully controlled conditions to allow the endogenous enzymes contained within the *M. capsulatus* cells, such as nucleases and proteases, to digest the components of the cell. This "self-digestion" process results in the production of various degradation products of the cell which may include peptides, amino acids, nucleotides, phospholipids, fatty acids, etc.

Suitable reaction conditions for hydrolysis and autolysis of *M. capsulatus* may be determined by one skilled in the art.

The number of intact *M. capsulatus* cells remaining in the lysate following cessation of the lysis technique should be negligible and/or any intact cells which are present should be substantially, e.g. essentially, non-viable (as defined herein). Thus, an *M. capsulatus* lysate of the invention is incapable of causing the colonisation of a subject by *M. capsulatus*. *M. capsulatus* lysates may be inactivated with any of the above-mentioned inactivation techniques, e.g. pasteurisation and/or UV, X-ray, gamma ray sterilisation.

One or more of the above-described lysis and/or inactivation techniques may be applied to a *M. capsulatus* cell, e.g. in the form of a culture thereof. A "culture" of *M. capsulatus* cells may encompass the entire contents of an *M. capsulatus* culture (e.g. the medium/substrate and the biomass) or the *M. capsulatus* cells isolated, at least partially, from such medium/substrate, in particular the water therein, e.g. by centrifugation or filtration.

A "culture" of *M. capsulatus* extends to the product obtained following the fermentation of *M. capsulatus* in a fermenter. Suitable fermenters for use in culturing *M. capsulatus* are those of the loop-type, such as those described in DK 1404/92, EP-A-418187 and EPA 306466 of Dansk Bioprotein, or air-lift reactors. Other fermenters may be used in culturing *M. capsulatus* and these include tubular and stirred tank fermenters.

The *M. capsulatus* for use in the invention may be cultured/fermented on any suitable medium and substrate. The exact nature of the growth medium used is not critical (e.g. nitrate mineral salts medium (NMS) or ammonium/mineral salts medium (AMS)) and a variety of suitable substrates may be used. Conveniently, *M. capsulatus* is cultured on or in a suitable medium (e.g. a medium with a nitrogen source (e.g. ammonia or nitrate) and a nutrient mineral solution) and said culture is supplemented with oxygen and a liquid and/or gaseous hydrocarbon, e.g. methane, methanol or natural gas.

Supplementation may conveniently be achieved with a gas mixture of about 20% to about 30% methane (e.g. about 20% to about 22%, 24%, 26% or 28%, or about 22%, 24%, 26% or 28% to about 30%), about 0.4% to about 2% (e.g. about 0.4% to about 0.6%, 0.8%, 1.0%, 1.2%, 1.4%, 1.6% or 1.8%, or about 0.6%, 0.8%, 1.0%, 1.2%, 1.4%, 1.6% or 1.8% to about 2.0%) carbon dioxide and, optionally, about 15% to about 25% (e.g. about 15% to about 17%, 19%, 21% or 23% or about 17% 19%, 21% or 23% to about 25%) oxygen, with the remainder made up of air. Any ranges which may be formed from the above recited range end-points are expressly contemplated.

Methanol may be provided in the culture medium up to a concentration of about 5% (v/v), e.g. up to about 1%, 0.5%, 0.1%, 0.05% or 0.01%.

Temperature may range of from about 40° C. to about 50° C., most preferably 45° C.±2° C. and pH may be about 6.0 to about 7.5, e. g. to 6.8±0.3. A number of such processes are well known and described in the art, for example in WO 01/60974, DK-B-170824, EP-A-418187 and EP-A-306466, the contents of which are herein incorporated by reference.

Following culture/fermentation the *M. capsulatus* cells may be separated from the medium by techniques well known in the art, e.g. centrifugation and/or filtration. Concentration of the *M. capsulatus* cells may be effected by centrifugation alone. Separation may be carried out at a temperature in the range of about 4° C. to about 70° C., e.g. from about 4° C. to about 50, 40, 30, 20, 15, 10, 8, 6 or 5° C. The size exclusion used during filtration will generally be in the range of about 0.1 to about 10 µm, e.g. about 0.2 to about 0.4 µm, i.e. microfiltration.

In other embodiments the above-described processing steps are applied to a culture of *M. capsulatus* which has been rendered non-viable, e.g. as defined above.

A lysate may be considered to be the direct product obtained from the application of a lysis technique to an *M. capsulatus* or a culture thereof, or a concentrated form thereof. Expressed differently, a lysate in accordance with the invention contains representatives of essentially all of the components of an *M. capsulatus* or a culture thereof which are not water molecules (which may be removed) in essentially the same relative proportions. In other words, a lysate of the invention has not been processed to remove particular components other than water.

Lysates may be concentrated by techniques well known in the art, e.g. centrifugation and/or filtration (e.g. ultrafiltration). Concentration of the lysis products may be effected by centrifugation alone. The size exclusion used during ultrafiltration will generally be in the range of about 100 kDa. However, filters having a MW cut-off in the range of from 10 to 100 kDa, e.g. about 20 kDa, may be used.

Alternatively or additionally the lysate may be dried, e.g. to a solid, e.g. powder form. Conveniently this may be by freeze drying or spray drying.

In certain embodiments, the *M. capsulatus* lysate or non-viable *M. capsulatus* of use in the invention substantially, e.g. essentially, dry, i.e. is substantially, e.g. essentially, water-free (moisture-free). This may be expressed as a water content of less than 15% w/w, e.g. less than 12, 10, 9%, 8%, 7%, 6%, 5%, 4.5%, 4%, 3.5%, 3%, 2.5%, 2%, 1.5% or 1% w/w as measured by weight loss on drying or chemically by the Karl Fischer method (United States Pharmacopeia; European Pharmacopoeia).

The subject may be any human or non-human vertebrate animal subject, e.g. a mammal, bird or fish, including livestock and companion animals, e.g. pigs, poultry (e.g. chickens, turkeys), cows, goats, sheep, horses, fish (e.g. salmon, trout, cod, halibut), dogs, cats and rodents, e.g. a mouse. Non-ruminant animals are of note. Preferably the subject is a human, in which case the term "patient" may be used interchangeably with the term "subject".

The subject may be of any age, e.g. an infant, a child, a juvenile, an adolescent or an adult, preferably an adult. In humans, an adult is considered to be of at least 16 years of age and an infant to be up to 2 years of age. In certain embodiments the subject will be an infant, in others it will be a child or an adult. The subject may have or be suspected of having or be or suspected of being at risk of dysbiosis A "normal" or "healthy" subject is a subject that is not considered to have a diagnosed or suspected illness or disease or other medical condition associated with GI tract dysbiosis. In preferred embodiments the subject will have reported being in full health, in particular full digestive health. A "normal" or "healthy" GI tract is a GI tract from such subjects. Alternatively put, a "normal" or "healthy" subject (or GI tract) is a subject/GI tract that does not have GI tract dysbiosis, e.g. as measured by the Dysbiosis Index described in Casén, C., et al, supra and and WO 2016/156251. In other embodiments a normal or healthy subject will be essentially free of serious illness or disease or other medical conditions, or at least is a subject that does not have observable or detectable symptoms of any recognised serious illness or disease. In other embodiments a normal or healthy subject will be free of all illness or disease or other medical conditions, or at least does not have observable or detectable symptoms of any recognised illness or disease. Preferably this reference to illness, disease or medical condition is a reference to an illness, disease or medical condition of the GI tract, in particular the intestinal tract.

The word "corresponding" is used to convey the concept that the subject to which the term is applied is the same as another instance of that subject. Thus the essential features that define that subject are shared by the other subject even though precise details may be unique. Alternative terms could be "matching", "analogous", agreeing", "equivalent" or "same as".

In accordance with the invention the lysates and non-viable forms of *Methylococcus capsulatus* may be administered to the subject in any convenient form or by any convenient means in order to achieve effective amounts in the GI tract, e.g. at least in the part of the GI tract which has dysbiosis to be treated. By effective amounts it is meant an amount sufficient to treat or prevent dysbiosis in accordance with the invention Delivery may therefore be by oral, rectal or intraintestinal routes. Oral administration is most convenient.

It may be most convenient to simply administer an effective amount of *Methylococcus capsulatus* of use in the invention in drinking water or another foodstuff, in particular a liquid foodstuff, of the subject. In certain embodiments the *Methylococcus capsulatus* may be provided as a convenient protein source in said foodstuff. However, in other embodiments, e.g. in the context of human use, it may be more acceptable to subjects undergoing treatment if *Methylococcus capsulatus* is provided in a form resembling a pharmaceutical dosage form.

The skilled man will be able to formulate non-viable forms of *Methylococcus capsulatus* and/or lysates of *Methylococcus capsulatus* into food additive, nutraceutical or pharmaceutical compositions that are adapted for oral, rectal or intraintestinal routes of administration according to any of the conventional methods known in the art and widely described in the literature.

When used in the raising of livestock ("food" animals), the *Methylococcus capsulatus* of use in the invention may be incorporated into conventional animal feeds (e. g. meal, pellets, extruded pellets, meat-based products, cereals, soya-based products, etc.) during production or manufacture in any suitable manner. Alternatively, the *Methylococcus capsulatus* of use in the invention may be provided in the form of a feed additive to be mixed with or applied to a conventional animal feed immediately prior to consumption by the animal in an amount sufficient to treat or prevent dysbiosis in the subject animals.

The *Methylococcus capsulatus* of use in the invention may also be provided in pet food in order to treat or prevent dysbiosis in pets. Accordingly, the material also finds use in the manufacture of a pet food or as a pet food additive. The term "pet food" as used herein generally refers to any food intended primarily for consumption by pets. Specifically, this includes nutritionally balanced food compositions which are intended to provide substantially the sole diet for the animal. Nutritionally-balanced foods will contain protein, carbohydrates, fats, vitamins and minerals in amounts sufficient for adequate growth and maintenance (i. e. health) of the animal.

As used herein the term "pet" is primarily intended to encompass cats and dogs, especially dogs. However, the product herein described may also be used as, in or as an additive to foods intended for consumption by any essentially domesticated or tamed animal or bird, such as rabbits, guinea pigs, tropical fish, birds, etc. The term "pet" is not intended to encompass livestock such as pigs, chickens, cows, etc., or any animal which is primarily bred for human consumption, e. g. fish such as salmon.

The term "pet food additive" as used herein generally refers to any product which is intended to be added to (e. g. incorporated into and/or applied to) a pet food, for example during the manufacturing process or immediately prior to consumption of the food. For example, the *Methylococcus capsulatus* of use in the invention may be dispersed within a pet food or within any component of a pet food (e. g. a gravy or sauce), or coated (either completely or partially) onto an exterior surface of the food. Alternatively, the *Methylococcus capsulatus* of use in the invention may be provided in the form of a pet food additive to be mixed with or applied to a conventional pet food immediately prior to consumption by the animal. For example, this may be liberally sprinkled or sprayed onto the surface of the food in an amount sufficient to treat or prevent dysbiosis in the subject animal.

Typical pet food compositions to which the biomass material may be added and/or applied include poultry or beef by-products, and soya-based preparations. In certain embodiments, compositions are those which are commercially sold and are nutritionally balanced.

Non-viable forms of *Methylococcus capsulatus* or a lysate of *Methylococcus capsulatus* should be employed in animal foods (both pet foods and feed intended for consumption by livestock) in an amount effective for the treatment or prevention of dysbiosis. Appropriate levels of incorporation of the material will depend on several factors, such as the animal species, age and size of the animal for which this is intended, etc. Suitable levels may readily be determined by those skilled in the art. Typically, when added to conventional animal feeds or pet foods, levels of incorporation in the range of from 1 to 40 wt. %, e. g. from 2 to 20 wt. %, may be used to treat or prevent dysbiosis.

For human subjects non-viable forms of *Methylococcus capsulatus* or a lysate of *Methylococcus capsulatus* may be incorporated into the normal diet as a dietary supplement or may be added to certain foods intended for human consumption in order to treat or prevent dysbiosis. Examples of food products which might contain an appropriate amount of the *Methylococcus capsulatus* of use in the invention include, for example, bakery products, meat products, dairy products and processed foods. The *Methylococcus capsulatus* of use in the invention may replace a portion of the animal proteins in the food. When provided in the form of a dietary supplement, the *Methylococcus capsulatus* of use in the invention may be a liquid. However, it might be more convenient to provide the *Methylococcus capsulatus* of use in the invention in the form of a powder which can be stored for long periods of time without degradation and which can be added to a food in the appropriate amount or which may be reconstituted into a liquid form (e.g. by the addition of water) immediately prior to consumption.

In other embodiments, the non-viable *Methylococcus capsulatus* or lysate of *Methylococcus capsulatus* of the invention may be incorporated, optionally together with other active agents (e.g. those discussed herein), with one or more conventional carriers, diluents and/or excipients, to produce conventional galenic preparations such as tablets, pills, granules (including enteric coated granules), lozenges, sachets, cachets, elixirs, suspensions, emulsions, solutions, syrups, aerosols (as a solid or in a liquid medium), sprays, soft and hard gelatine capsules, suppositories, sterile injectable solutions, sterile packaged powders, and the like. Enteric coated solid or liquid compositions, e.g. enteric coated tablets and enteric coated granules (which may be provided in an enteric-coated capsule or in a non-enteric-coated capsule i.e. in which the coating may or may not be an enteric coating) may be especially effective are all of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, buffering agents, and the like.

Additional therapeutically active agents may also be included in the pharmaceutical compositions.

Parenterally administrable forms, e.g. solutions suitable for delivery via the intraintestinal route, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975)), which is explicitly incorporated by reference herein in its entirety. The solutions can contain preservatives, antimicrobial agents, buffers and antioxidants conventionally used for parenteral solutions, excipients and other additives which are compatible with the biopolymers and which will not interfere with the manufacture, storage or use of products.

Simple sterile liquid compositions comprising *Methylococcus capsulatus* may be especially convenient for intraintestinal use. Such formulations may consist of sterile water and *Methylococcus capsulatus*.

Solid or liquid formulations of *Methylococcus capsulatus* may be provided with an enteric coating that prevents degradation in the stomach and/or other parts of the upper GI tract but permits degradation in the lower GI tract, e.g. the small intestine. Such coatings are routinely prepared from polymers including fatty acids, waxes, shellac, plastics, and plant fibres. Specific examples thereof include but are not limited to methyl acrylate-methacrylic acid copolymers, methyl methacrylate-methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), cellulose acetate trimellitate, and sodium alginate polymer. Enteric coated tablets and enteric coated granules (which may be provided in an enteric-coated capsule or in a non-enteric coated capsule) are of particular note. Enteric coated granules may be prepared in accordance with the teachings of WO 1989/008448 and Al-Khedairy, E. B. H, 2006, Iraqi J. Pharm. Sci., Vol. 15 (1) 49, the contents of which are incorporated herein by reference, although the skilled person would be aware of further alternative techniques which may be used.

The relative content of non-viable *Methylococcus capsulatus* or lysate of *Methylococcus capsulatus* in the compositions of the invention can vary depending on the dosage required and the dosage regime being followed but will be sufficient to achieve an effective amount at the target treatment area, taking account of variables such as the physical size of the subject to be treated, the nature of the subject's particular ailments, and the precise location and identity of the target treatment area. The skilled person would know that the amounts of the *Methylococcus capsulatus* of use in the invention can be reduced if a multiple dosing regime is followed or increased to minimise the number of administrations or applications.

The *Methylococcus capsulatus* of use in the invention may be used at a daily dose of about 0.1 to about 500 g/kg, e.g. about 0.1, 1, 10, 50, 100, 150, 200, 250, 300, 350, 400 or 450 to about 500 g/kg, or about 0.1 to about 1, 10, 50, 100, 150, 200, 250, 300, 350, 400 or about 450 g/kg which may be administered at one or more times per day (e.g. bis daily) and in one or more dosage forms or administration events (e.g. two tablets bis daily). Any ranges which may be formed from the above recited range endpoints are expressly contemplated.

A representative tablet to be used to administer a non-viable *Methylococcus capsulatus* or a lysate of *Methylococcus capsulatus* to the lower GI tract may contain up to 99%, up to 95%, 90%, 85% or 80%, e.g. 50 to 95%, 55 to 95%, 60 to 95%, 65 to 95%, 70 to 95%, 75 to 95%, 80 to 95%, 85 to 95%, 90 to 95%, 50 to 90%, 50 to 90%, 55 to 90%, 60 to 90%, 65 to 90%, 70 to 90%, 75 to 90%, 80 to 90%, 85 to 90%, 50 to 90%, 55 to 85%, 60 to 80% or, 65 to 75% w/v or w/w of a non-viable *Methylococcus capsulatus* or a lysate of *Methylococcus capsulatus*, the remainder being comprised of pharmaceutically acceptable excipients and/or other active agents if being used.

An enteric coated tablet may also be effective in administering *Methylococcus capsulatus* of use in the invention to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of a non-viable *Methylococcus capsulatus* or a lysate of *Methylococcus capsulatus*, the remainder being comprised of pharmaceutically acceptable excipients, including the enteric coating (e.g. polymers including fatty acids, waxes, shellac, plastics, and plant fibres) and/or other active agents if being used.

Enteric coated granules may also be effective in administering *Methylococcus capsulatus* of use in the invention to the lower GI tract. Such granules may be provided in a capsule which itself may or may not be provided with an enteric coating. A representative enteric coated granule may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of a non-viable *Methylococcus capsulatus* or a lysate of *Methylococcus capsulatus*, the remainder being comprised of pharmaceutically acceptable excipients, including the enteric coating (e.g. polymers including fatty acids, waxes, shellac, plastics, and plant fibres) and/or other active agents if being used.

A representative aqueous solution for intraintestinal routes will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of a non-viable *Methylococcus capsulatus* or a lysate of *Methylococcus capsulatus*, the remainder being comprised of water and pharmaceutically acceptable excipients and/or other active agents if being used.

Drinking water/foodstuff containing the *Methylococcus capsulatus* of use in the invention may contain 1 to 25%, e.g. 1 to 20%, 1 to 15%, 1 to 10%, 1 to 5%, 2 to 25%, 2 to 20%, 2 to 15%, 2 to 10%, 2 to 5%, 5 to 25%, 5 to 20%, 5 to 15%, 5% to 10%, 10 to 15%, 10 to 20%, 10 to 25%, 15 to 20%, or 15 to 25% w/v of a non-viable *Methylococcus capsulatus* or a lysate of *Methylococcus capsulatus*, the remainder being comprised of water/foodstuff.

The invention will be further described with reference to the following non-limiting Examples in which:

FIG. 1 presents a chart showing the dominating genera in the GI tract microbiota of test animals fed differing diets as described in Example 2.

Figure 2:
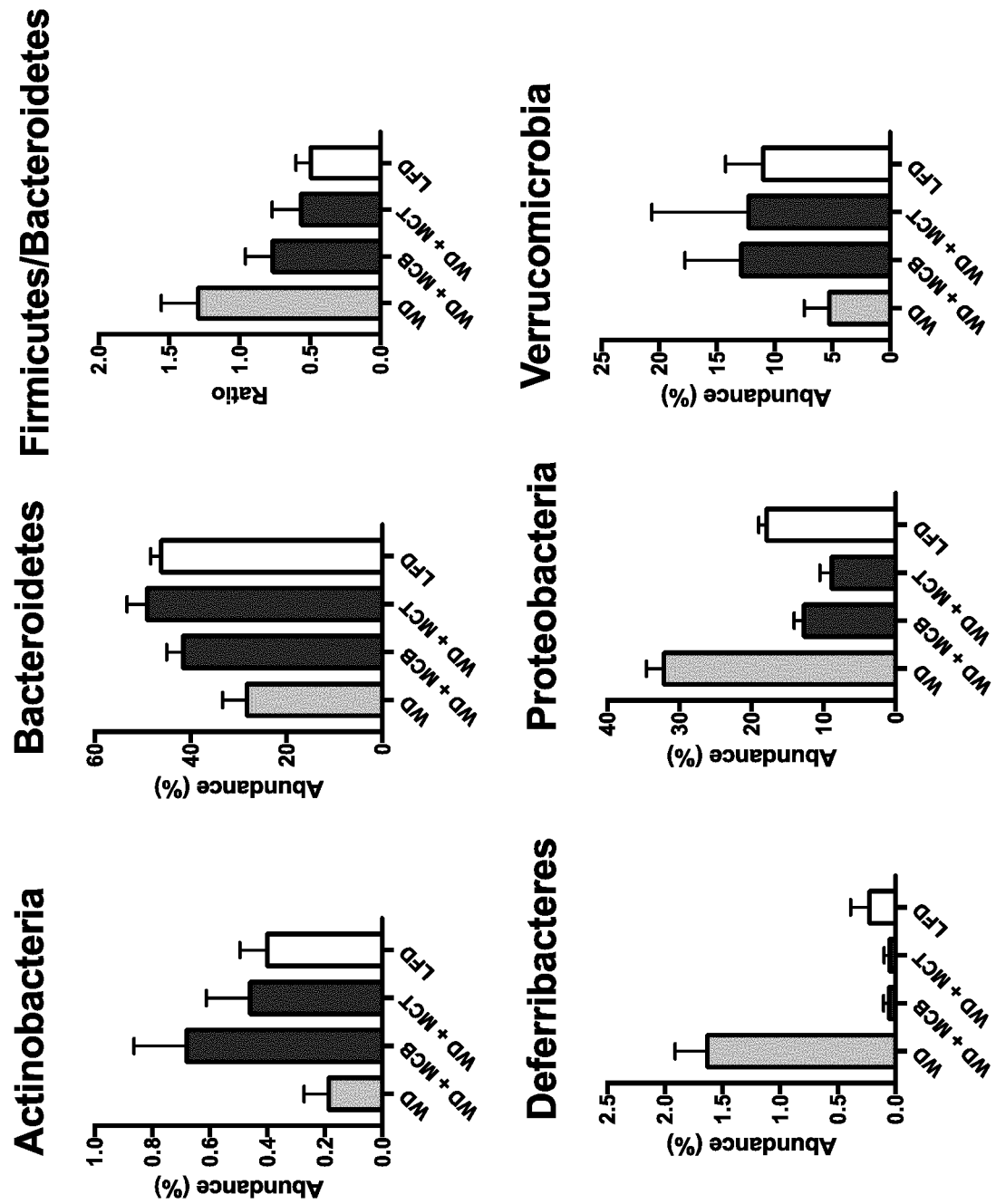

FIG. 2 present charts showing the levels of a selection of phyla in the GI microbiota of test animals fed differing diets as described in Example 3.

Figure 3:
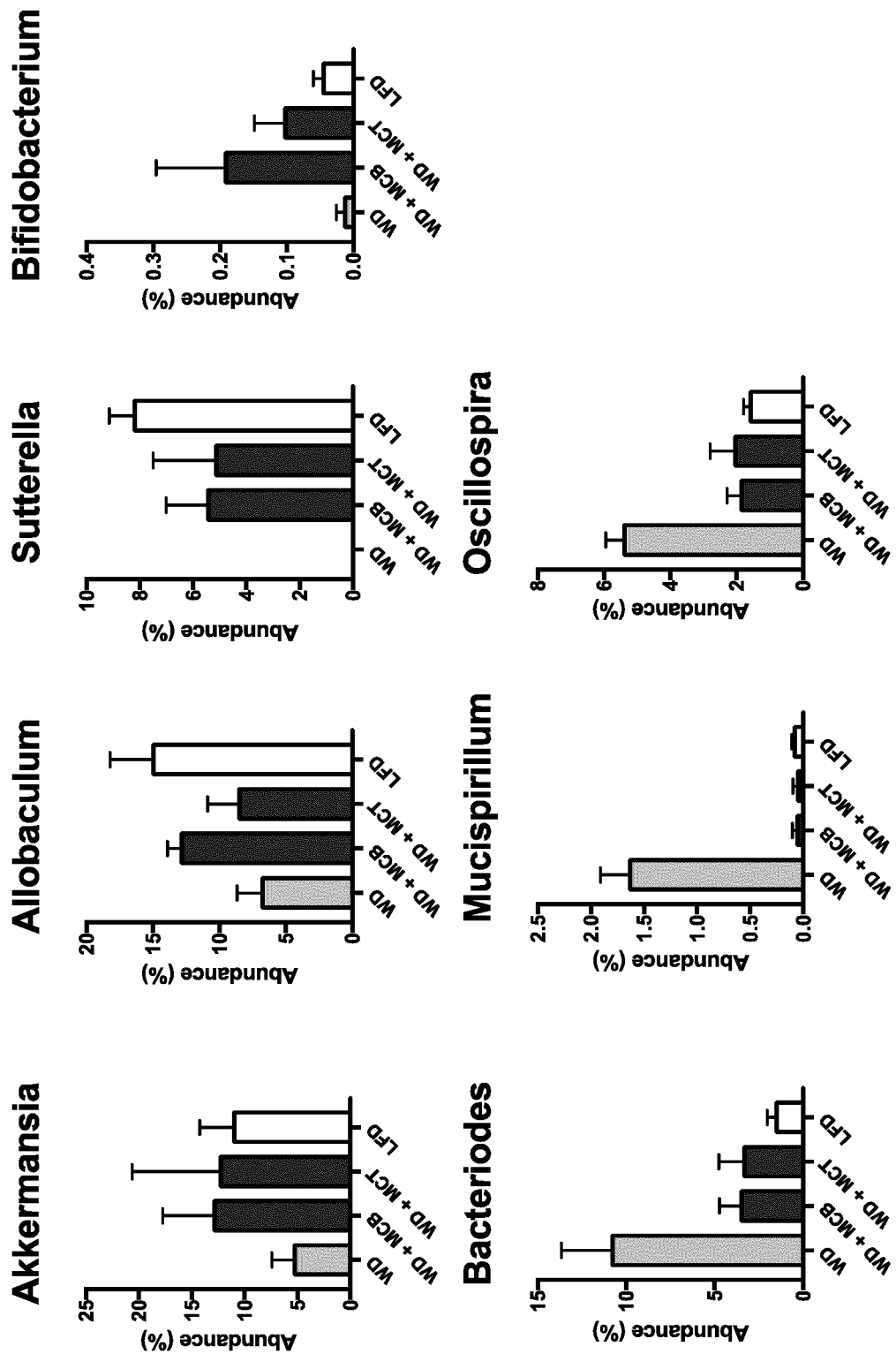

FIG. 3 presents charts showing the levels of a selection of genera in the GI microbiota of test animals fed differing diets as described in Example 3.

Figures 4, 5:
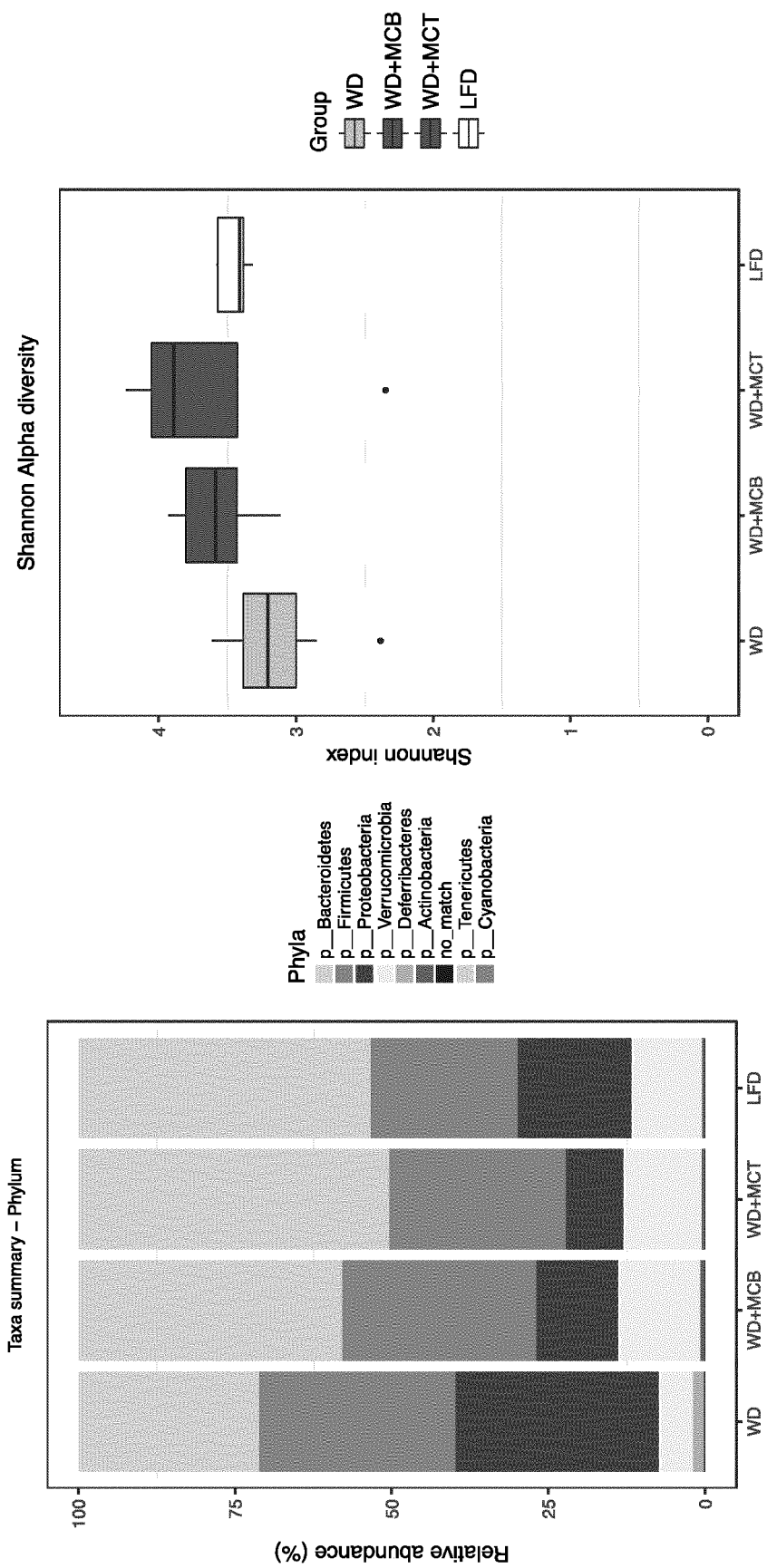

FIG. 4 presents a taxa summary plot at phylum level of the GI tract microbiota of test subject animals fed differing diets as described in Example 3.

FIG. 5 presents a chart showing the Shannon Index (alpha diversity/richness) of the GI tract microbiota of test subject animals fed differing diets as described in Example 3.

FIG. 6 presents PCoA plots with UniFrac distances of the GI tract microbiota of the test subject animals before change in diet (Wk20), halfway through treatment (3 weeks; Wk23), end of treatment (5 weeks; Wk25), as described in Example 3. (A) unweighted and (B) weighted.

FIG. 7 presents PCoA plots with UniFrac distances of the GI tract microbiota (faecal (F) or small intestine (SI)) of the test subject animals before change in diet (Wk), and at weeks 2, 4, 6, 20 and 25 (Wk2, Wk4, Wk6, Wk20 and Wk25) under experimental diet for two experiments (1) and (2), respectively, as described in Example 4. (A) unweighted and (B) weighted.

Figure 8A:
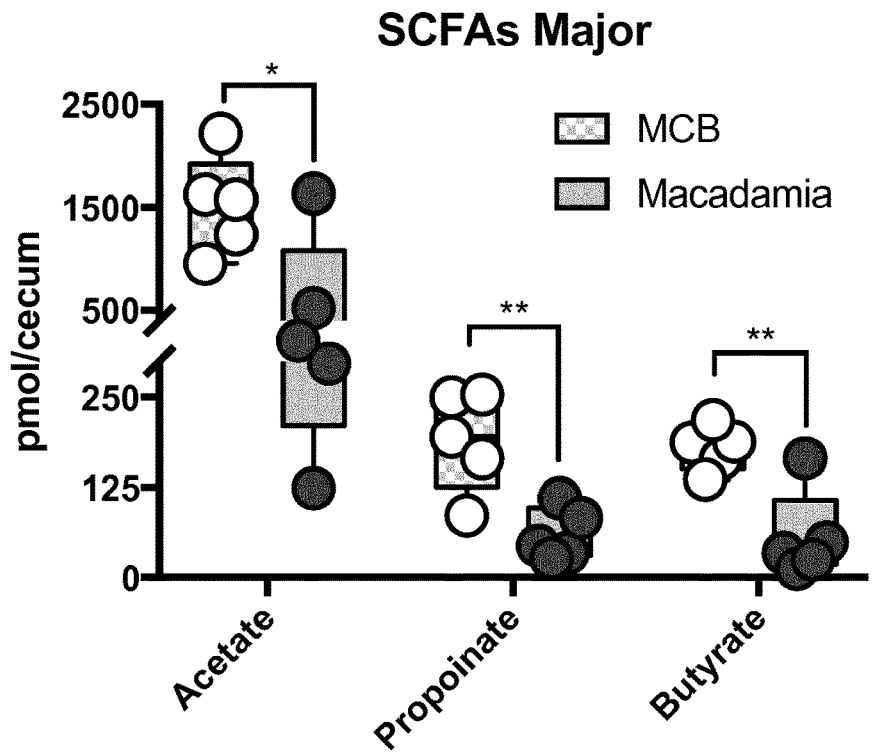
Figure 8B:
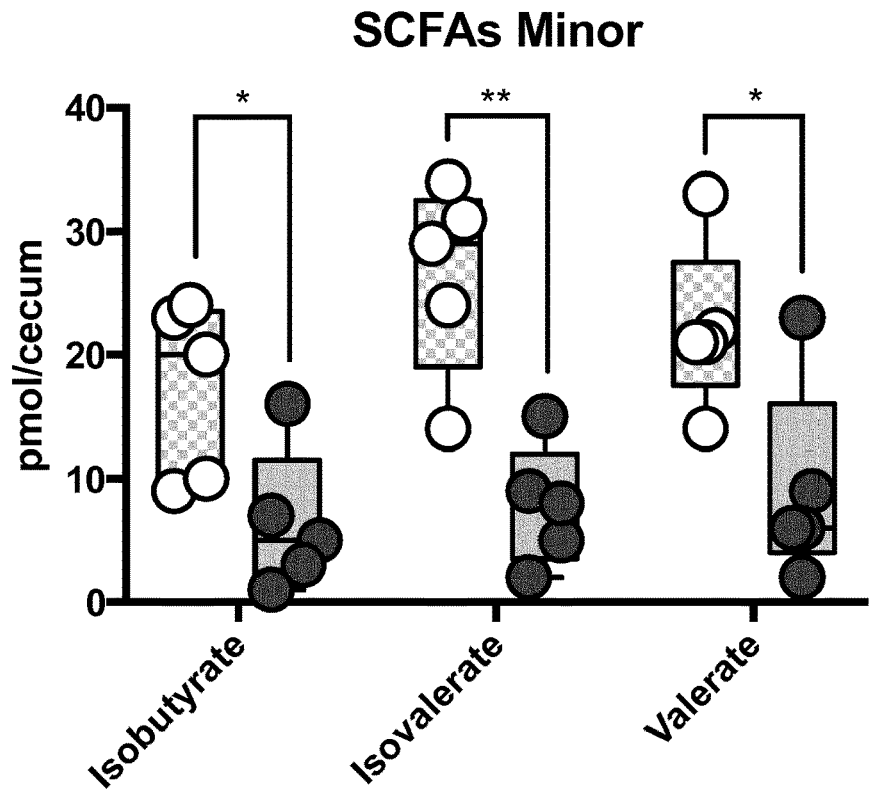

FIG. 8 presents charts showing the amounts of caecal small chain fatty acids in mice fed MCB (white circles, checkered bars) or macadamia oil (grey circles, grey bars) modified western diets, as described in Example 4. FIG. 8A shows a consistent upregulation of both the three major and minor classes of SCFAs in the cecum of WD-MCB fed mice compared to WD-Macadamia fed mice further supporting a beneficial health impact on dietary inclusion of MCB extracts. FIG. 8B shows the same for the three minor classes.

FIG. 9 shows various data representations providing evidence that MCB feeding of mice stimulates the induction of gut specific regulatory T cells and IL17 expression, as described in Example 5. In FIG. 9A, the proportion of RORgt+ Tregs, a microbiota induced Treg lineage (iTreg) with immense stability and immune resolving capabilities, was increased more than 2-fold in the colonic lamina propria of WD-MCB fed mice (p<0.001). FIG. 9B shows that stimulated iTregs expressed ample amounts of IL-17, while unstimulated cells, as expected, displayed hampered IL-17 expression. FIGS. 9C-9F demonstrate that proportion of IL-17+ cells within this cell subset was further increased by ~2.5-fold in WD-MCB fed mice compared to WD-Macadamia fed mice (p>0.0001). FIGS. 9G-9L show a similar phenotype in the small intestine of experimental mice, where RORgt+ iTregs in WD-MCB fed mice reached ~4-5-fold increase compared to WD-Macadamia fed control mice (FIG. 9G, p<0.0001). FIG. 9M-9N show analysis of the liver of the experimental mice by H&E stain. Mice fed WD-MCB unveiled diminished NAFLD-activity compared to mice fed WD-Macadamia (p<0.01).

EXAMPLES

Example 1

Cultivation of *M. capsulatus* and Preparation of Lysate

*Methylococcus capsulatus* (Bath) NCIMB 11132 or *Methylococcus apsulatus* (Texas) NCIMB 11853 were used to produce single-strain bacterial meals (freeze-dried lysates). Nitrate mineral salts (NMS) medium was used for all types of cultivations. *M. capsulatus* culture aliquots were frozen in liquid nitrogen and stored at −80° C. Cultivations on agar plates and in shake flasks were performed at 45° C. in an atmosphere of 75% air, 23.25% $CH_4$, and 1.25% $CO_2$. Shake flask cultures were incubated in an orbital shaker incubator at 200 rpm. Continuous cultivation was carried out in a 3-liter bioreactor (ADI Autoclavable bioreactor systems; Applikon, Schiedam, The Netherlands) with a working volume of 2 litres. Cells precultivated in shake flasks were used to inoculate the bioreactor to an optical density at 440 nm ($OD_{440}$) of 0.1. The temperature was maintained at 45° C., stirring was set to 650 rpm, and a culture pH of 6.8 was maintained by automatic addition of 2.5 M NaOH. A gas mixture of 55% air, 24% methane, 20% $O_2$, and 1% $CO_2$ was sparged into the bioreactor at a constant flow of 0.064 volumes of gas per volume of liquid and minute (vvm). The continuous culture was started after an initial batch phase, and the dilution rate was set to 0.01 $h^{-1}$. The $OD_{440}$ at steady state was generally sustained at approximately 10. Culture effluent was collected, and cells were harvested by centrifugation. Bacterial cell walls were disrupted by the use of a French press before freeze-drying of the material.

Example 2

Microbiota Analysis of the GI Tract of Female C57BL/6N Tac Mice Fed *M. capsulatus* Lysate Female C57BL/6N Tac mice (age 5 to 6 weeks; weight, 15 to 18 g) from Taconic (Ry, Denmark) and with conventional microbiological status were used. The animals were split in three groups with four animals per group. For 14 days the animals were fed ad libitum a control diet based on the AIN-93G standard western diet or an experimental diet where the casein content (200 g/kg of body weight) and corn starch (54 g/kg) were exchanged with 200 g/kg freeze-dried lysate of *M. capsulatus* Bath (Diet 1) or *E. coli* Nissle 1917 (Diet 2). The feeding experiment lasted for 14 days. Then the animals were sacrificed and the intestines taken out for further analysis.

DNA was extracted from caecal contents by mechanical lysis and QiaAmp DNA Stool kit. PCR was performed in triplicates. The V4 region of the 16S rRNA gene was amplified with region-specific primers. The sample pool was purified and quantified using Quant-iT Picogreen ds DNA, diluted to proper concentration and sequenced on a MiSeq (Illumina) according to the protocol provided by Illumina. Sequencing data were subjected to QIIME analysis.

FIG. 1 shows the differences between the dominating genera in the microbiota of the test animals fed the different diets. As can be seen Diets 1 and 2 induce variation in the microbiota profile of the GI tract of the experimental subjects. Compared to mice fed on the control diet, Diet 1 (freeze-dried lysate of *M. capsulatus* (Bath)) shows increases in the levels of both Akkermansia and *Allobaculum* species, which have separately been associated with positive effects in obese subjects and subjects with type 2 diabetes. Diet 1 also shows increased levels of *Clostridium* species, which have been suggested to improve intestinal barrier function Example 3

Microbiota Analysis of the GI Tract of Male C57BL/6J Mice Mice Fed *M. capsulatus* Lysates Male C57BL/6J mice (age 6 to 8 weeks; weight ~25 g) from Taconic (Ry, Denmark) and with conventional microbiological status were used. The animals were acclimated on a regular chow diet for two weeks prior to the feeding experiment and subsequently fed an AIN-93G standard western diet with soy oil as fat source (D12079*mod, Ssniff spezial diäten) (WD) or a low fat reference diet (LFD) for 20 weeks. Here, western diet fed mice were stratified by fat-mass and divided into two experimental groups; one continuing to receive the aforementioned standard western diet and one receiving an experimental diet, where the casein content (200 gram per kg diet) was exchanged with freeze-dried lysate of *M. capsulatus* (Bath) or freeze-dried lysate of *M. capsulatus* (Texas) (WD+MCB and WD+MCT, respectively). The experimental feeding lasted for 35 days. The animals were then euthanised in 5 h fasted/feed-deprived state and the intestine, plasma, liver, and adipose tissues were taken out for further analysis. Metabolic state was/or metabolic states were determined in all mice prior to diet change by magnetic resonance (MR) body scan, fasted blood glucose, fasted insulin levels and insulin tolerance test. All mice were MR-scanned to determine their body composition, prior to diet change and 3 and 5 weeks post diet change. Faeces for analyses of microbiota composition were sampled at every scan. Weight development was monitored weekly and feed intake twice weekly.

Fresh faecal samples were collected and immediately snap frozen in liquid nitrogen. Bacterial DNA from faecal samples was extracted using a NucleoSpin soil kit (Macherey-Nagel) according to manufacturer's instructions. The PCR-based library formation was performed using 10 ng bacterial DNA, 0.2 µM of each barcoded forward and reverse primer, 0.2 mMdNTPs and 0.5 units Phusion high fidelity DNA polymerase (Thermo Scientific) in a total volume of 25 µl. To target the 16S rRNA gene's variable region 4 (V4) barcoded Illumina 515F and 806R primers with Illumina adaptor sequences at the 5' end were used.

Cycling conditions were as follows: 98° C. for 30 seconds followed by 35 cycles of 98° C. for 5 s, 56° C. for 20 s and 70° C. for 20 s. Subsequently, samples were pooled and sequenced using an Illumina MiSeq. Raw sequencing data were processed using the QIIME software including de novo-OTU picking, chimera-checking, and taxonomical assignment using the Greengenes database.

Principal Coordinates Analysis (PCoA) was based on weighted or unweighted UniFrac distance. Centroids were calculated as mean value per group per time point. Individual samples were connected with the centroids in the plot by lines. Alpha diversity was calculated using Shannon Index and visualised with boxplots where the lower and upper hinges correspond to the first and third quartiles (the 25th and 75th percentiles).

As shown in FIGS. 2 and 3, obese mice on either of the *M. capsulatus* supplemented high fat diets had a profile of bacteria levels more approaching that of the mice on the low fat diet than the mice on the unmodified high fat diet. This is observed at the genus (FIG. 3) and the phylum (FIG. 2) level.

FIG. 4 presents a taxa summary plot at phylum level showing how feeding mice with the high fat/high sugar "Western" diet with casein (CAS) rather than a low fat diet (LFD) induces clear changes in the gut microbiota composition at phylum level. Exchanging casein in the diet with *M. capsulatus* (Bath) or *M. capsulatus* (Texas) for 5 weeks is able to reverse/reduce this microbial imbalance to a profile similar to that which is seen in the healthy LFD-fed mice.

FIG. 5 shows using the Shannon Index the alpha diversity/richness of GI tract microbiota in animals fed the differing diets. Feeding mice with high fat "Western" diet decreased richness of the gut microbiota compared to the mice fed LFD. Adding *M. capsulatus* (Bath) or (Texas) to the high fat/high sucrose diet increases and reestablishes the richness of the gut microbiota within 5 weeks of treatment.

Figure 6A:
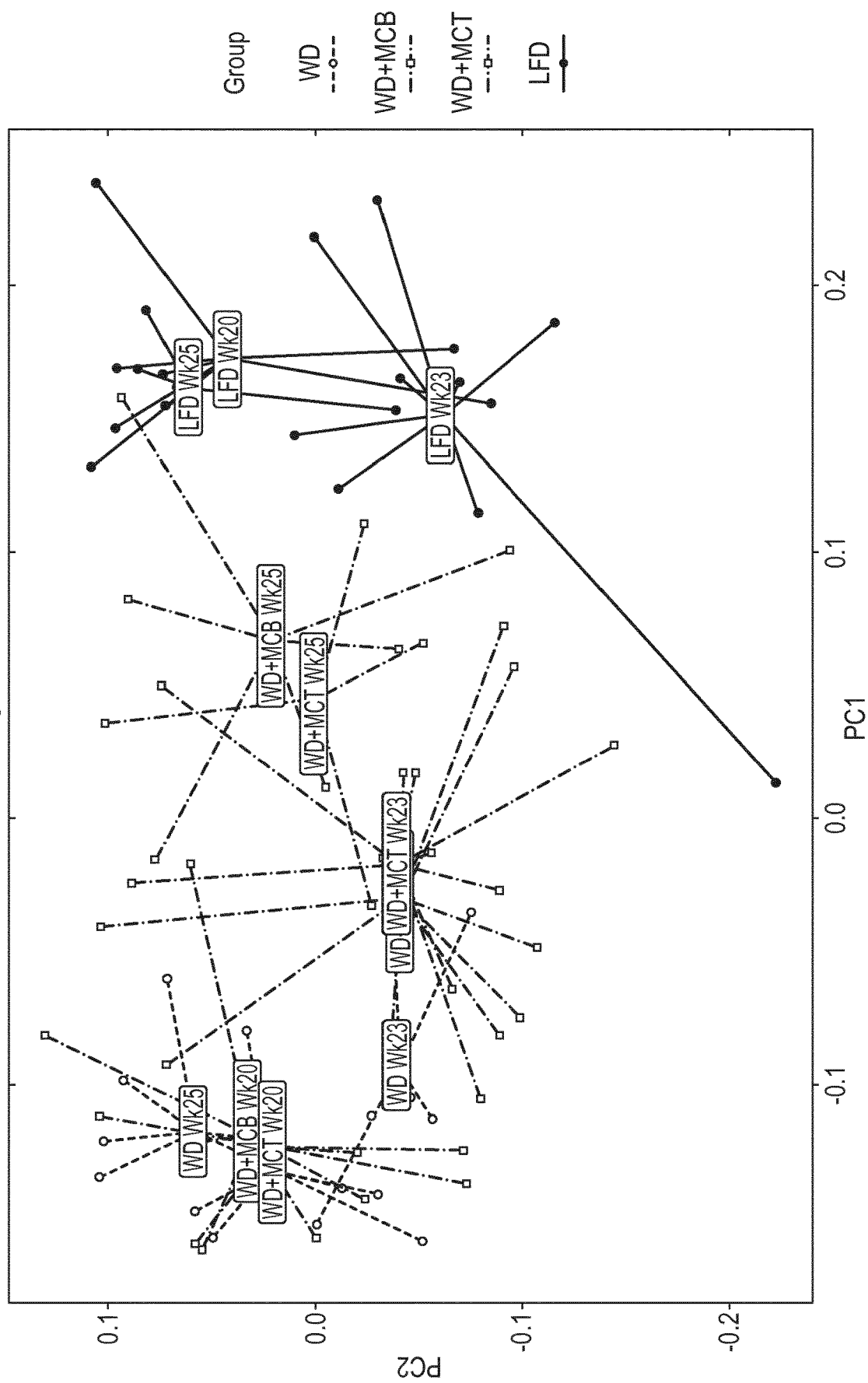

FIGS. 6A and B present PCoA plots with weighted or unweighted UniFrac distances showing how the microbiota of the WD-fed mice differ from the LFD-fed and how the exchanging casein with *M. capsulatus* (Bath) or (Texas) modifies the microbiota composition towards that seen in the healthy LFD-fed mice over the time period of the experiment.

Example 4

Microbiota Analysis of the GI Tract of Male C57BL/6J Mice Mice Fed *M. capsulatus* (Bath and Texas) Lysates and Gas Chromatography Analysis of Short Chain Fatty Acids in Cecal Samples Male C57BL/6J mice (age 6 to 8 weeks; weight ~25 g) from Taconic (Ry, Denmark) and with conventional microbiological status were used. The animals were acclimated on a low fat reference diet (LFD) for two weeks prior to the feeding experiment and subsequently fed an AIN-93G standard western diet with soy oil as fat source (D12079*mod, Ssniff spezial diäten) (WD) for 12 weeks. Here, WD fed mice were stratified by fatmass and divided into five experimental groups; one continuing to receive the aforementioned standard WD (WD), one returning to the low fat reference diet (LFD), one receiving an experimental diet, where the casein content (200 gram per kg diet) was exchanged with freeze-dried lysate of *M. capsulatus* (Bath)+added 5% casein to mirror the protein concentration of control mice (WD+MCB), one receiving an experimental diet, where the casein content (200 gram per kg diet) was exchanged with freeze-dried lysate of *M. capsulatus* (Texas)+added 5% casein to mirror the protein concentration of control mice (WD+MCT) and one receiving the WD with 5% added Macadamia oil to mimic the lipid content of the MCB abd MCT experimental groups (Macadamia). The experimental feeding lasted for 25 weeks. The animals were then euthanised in 5 h fasted/feed-deprived state and the intestine, plasma, liver, and adipose tissues were taken out for further analysis. Metabolic state was/or metabolic states were determined in all mice prior to diet change by magnetic resonance (MR) body scan, fasted blood glucose, fasted insulin levels and insulin tolerance test. All mice were MR-scanned to determine their body composition, prior to diet change and at weeks 2, 4, 6, 20 and 25 (Wk2, Wk4, Wk6, Wk20 and Wk25) post diet change. Faeces for analyses of microbiota composition were sampled at every scan. Weight development was monitored weekly and feed intake twice weekly.

Microbiota analysis was performed as described above. For gas chromatography analysis, caecal samples collected from the experimental mice were dispersed in MilliQ water and transferred to 2 ml tubes (Sarstedt, Germany) with 2 (2-3 mm) glass beads. Samples were homogenized in Fastprep96 (MP Biomedicals) for 40 sec at 1800 rpm. 2% formic acid were added with 500 µM 2-methylvaleric acid (internal standard). Samples were centrifuged at 13 000 rpm for 10 min. 300 µl supernatant was added to spin columns (VWR, with 0.2 µm filter) and centrifuged at 10 000 rpm for 5 minutes. The eluates were transferred to 300 µl GC vials. The samples were run on a Trace 1310 gas chromatograph with autosampler (ThermoFischer Scientific) equipped with a Stabilwax DA 30 m column (Restek) and a flame ionization detector.

Figure 7B:
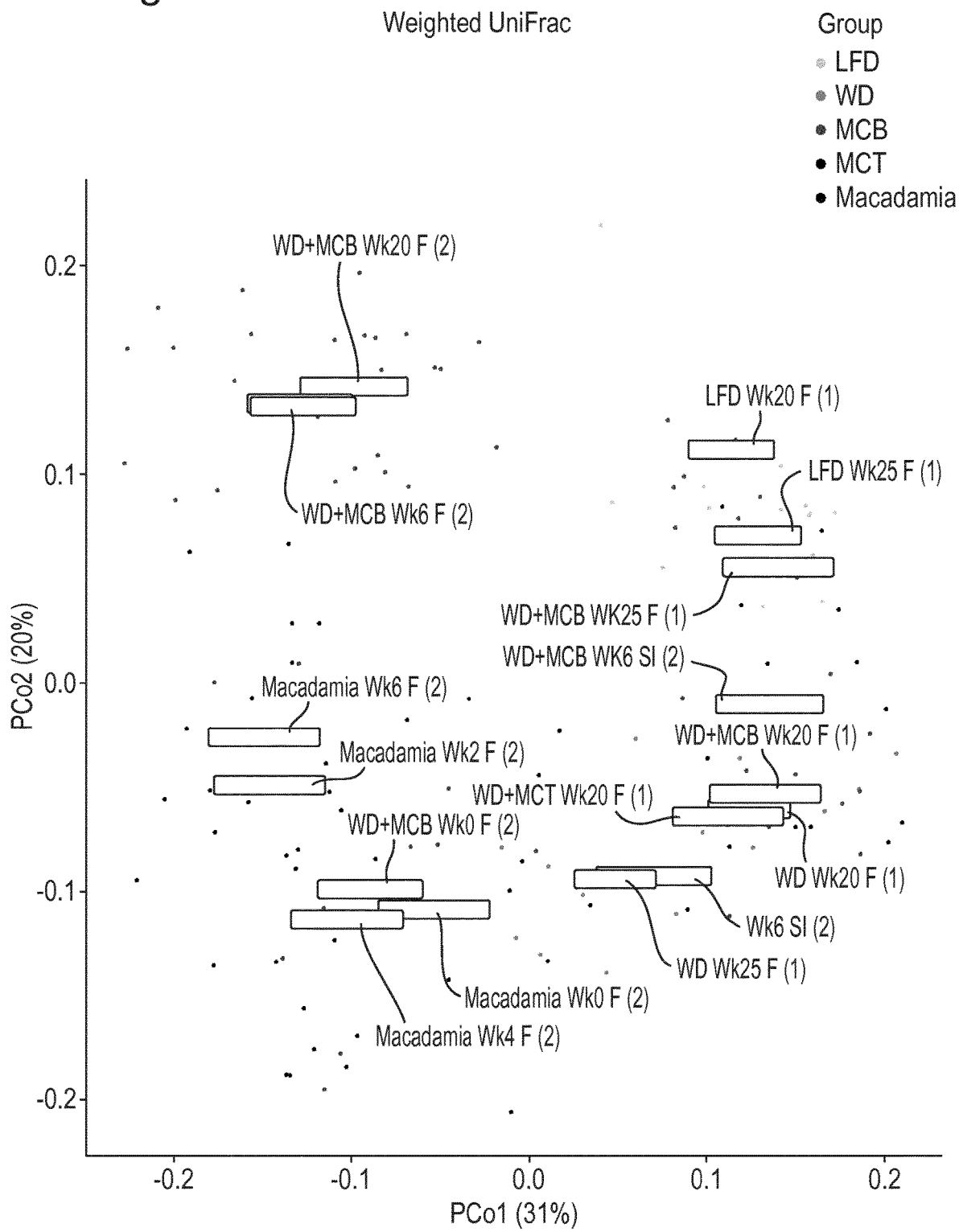

With focus on the dynamic interaction between gut immunity and commensal microbes, we analysed the gut microbiota of experimental mice as described above. The nature of our study design allowed us to follow the development in gut microbial composition from before diet change and throughout the intervention. Bi-weekly collected fecal and small intestinal samples revealed high similarity between groups at week 0 (when all mice were fed WD-reference), whereas a clear separation was observed already after 2 weeks on experimental diets—low fat diet (LFD), macadamia oil supplemented WD (Macademia), *M. capsulatus* (Bath) lysate modified WD (MCB) and *M. capsulatus* (Texas) (MCT) lysate modified WD (FIGS. 7A and 7B).

Interestingly, WD-Macadamia fed mice exhibited a highly stable microbiome signature in samples obtained before and after diet intervention, indicating that the added lipid source did not influence intestinal ecology. In contrast to this observation, we noted a pronounced shift in microbial diversity in mice fed WD-MCB and WD-MCT, with a particular and stable increase in the abundance of *Allobacullum* and *Barnesiella* genera as well as unclassified *Bacteroidetes* species countered by annulment of several *Clostridia* genera (data not shown).

Dietary nutrients—particularly fibres and to a lesser extent amino acids and peptides escaping digestion in the small intestine—are metabolised by the colonic and cecal microbiota. The metabolites, oligosaccharides and monosaccharides are then fermented into bioactive short chain fatty acid (SOFA) end-products, primarily acetate, propionate and butyrate. The three mentioned classes of SCFAs have vast impact on host physiology. Apart from promoting T cell differentiation into both effector and regulatory T cells depending on the immunological milieu (Park et al, 2015, Mucosal Immunology, Vol 8(1), 80-93), butyrate is more specifically used as growth substrate by healthy colonocytes while inhibiting carcinogenesis (Flint et al; 2012, Nature Reviews Gastroenterology & Hepatology, Vol 9, 577-589), hence facilitating improved gut health. The highest levels of SOFA are found in the cecum and proximal colon. We therefore investigated if cecal SCFAs levels were different between groups. We found a consistent upregulation of both the three major classes (FIG. 8A) and the three minor classes (FIG. 8B) of SCFAs in the cecum of WD-MCB fed mice compared to WD-Macadamia fed mice further supporting a beneficial health impact on dietary inclusion of MCB extracts.

Thus, it may be seen from these data that the microbiota of the WD-fed mice differ from the LFD-fed and that exchanging casein with *M. capsulatus* (Bath) or (Texas) modifies the microbiota composition towards that seen in the healthy LFD-fed mice over the time period of the experiment. Moreover, feeding with *M. capsulatus* (Bath) modified WD increases cecal SOFA levels compared to WD-Macadamia feeding.

Example 5

Flow Cytometry Analysis of the GI Tract of Male C57BL/6J Mice Mice Fed *M. capsulatus* Lysates Eight week old Male C57BL/6J mice (weight ~25 g) from Janvier Labs (France) with conventional microbiological status were used. The animals were acclimated on a low fat reference diet (LFD) for two weeks prior to the feeding experiment and subsequently fed an AIN-93G standard western diet with soy oil as fat source (D12079*mod, Ssniff spezial diäten) (WD) for 12 weeks. Here, WD fed mice were stratified by fatmass and divided into three experimental groups; one (Group B) continuing to receive the aforementioned standard WD, one receiving an experimental diet, where the casein content (200 gram per kg diet) was exchanged with freeze-dried lysate of *M. capsulatus* (Bath)+ added 5% casein to mirror the protein concentration of control mice (Group C), and one with 5% added Macadamia oil to mimic the lipid content of the experimental Group C (Group E). The experimental feeding lasted for 42 days. The animals were then euthanized in either fed state (n=4 per group) for flow cytometry analysis, or 5 h fasted/feed-deprived state (n=5 per group) where the intestine, plasma, liver, and adipose tissues were taken out for further analysis. Metabolic state was were determined in all mice prior to diet change by magnetic resonance (MR) body scan, fasted blood glucose, fasted insulin levels, response to oral glucose challenge and glucose stimulated insulin secretion. All mice were MR-scanned to determine their body composition, prior to diet change and 2, 4 and 6 weeks post diet change. Faeces for analyses of microbiota composition were sampled at every scan. Weight development was monitored weekly and feed intake twice weekly.

We characterized various T cell subset in both the small-intestinal and colonic lamina propria lymphocytes (LPLs) based on the staining panel recited in Table 1. Cells (LPLs) were isolated essentially as previously described in the literature. In short, intestinal pieces were incubated for 4×20 to 6×20 minutes in calcium- and magnesium-free (CMF) HBSS supplemented with 10% FCS and 10 mM HEPES (GIBCO BRL; Life Technologies, Paisley, Scotland, United Kingdom) (HBSS-10), containing 5 mM EDTA at 37° C. on an orbital shaker (125 rpm). Tissue pieces were washed and digested with collagenase type VIII (100 U/ml; Sigma-Aldrich) in RPMI supplemented with 10% FCS and 10 mM HEPES (RPMI-10) at 37° C. for 1 hour, twice. Flow cytometry was performed according to standard procedures. Dead cells (propidium iodide+) and cell aggregates (identified on FSC-A versus FSC-W scatterplots) were excluded from all analyses. Data acquisition was performed on a LSRII (BD Biosciences) and analyzed by using FlowJo software (Tree Star).

TABLE 1

Flow cytometry staining panel.

| P2 T cell panel | Fluorochrome | Dilution |
|---|---|---|
| IL-17A (TC11-18H10.1; Biolegend) | FITC | 1/200 |
| RORg (B2D; eBio) | PE | 1/200 |
| TCRb (H57-597; BD) | PECF594 | 1/200 |
| IL-22 (JOP; eBio) | PerCPCy5.5/PerCPeF710 | 1/100 |
| T-bet (eBio4B10) | PECy7 | 1/200 |
| TCRgd (GL3; Biolegend) | BV421 | 1/200 |
| Live/dead aqua + CD8a (53-6.7) | BV510 | 1/1000 |
| IFNg (XMG1.2; Biolegend) | BV605 | 1/100 |
| NK1.1 (PK136; Biolegend) | BV785/786 | 1/200 |
| FoxP3 (FJK-16S); eBio | APC | 1/100 |
| CD45 (30F11;eBio) | AF700 | 1/200 |
| CD4 (GK1.5, eBio) | APCeF780 | 1/200 |

Diet in general, and commensal microbes in particular, shape the gastrointestinal immune system, and have the potential to cross talk to glucoregulatory organs. As such we sought to evaluate if the positive metabolic consequences of feeding mice MCB extracts were linked to specific immune alterations.

IL-17 has emerged as a pleiotropic cytokine in line with IL-6, IL-18 and IL-22, and can thus augment non-alcoholic fatty liver disease (NAFLD) when expressed intra hepatically but also protect against the same disease when expressed by gut-specific immune cells. We therefore sought to identify the cellular origin of cytokine secretion and accordingly analysed the immune profile of small intestine (SI) and colonic lamina propria in a subset of experimental mice (n=4/group) using multicolour flow cytometry with phenotypic characterization of innate lymphoid cells class 3 (ILC3), natural killer (NK) cells, and T cells-including regulatory- and γδ T cells.

Both numbers of ILC3 and NK cells as well as their cytokine profile were similar between groups throughout the gastrointestinal tract. The same was true for the numbers of colonic $CD4^+$, γδ, and classical $Foxp3^+$ regulatory T cells ($nT_{regs}$) (data not shown). On the other hand, the proportion of $RORγt^+$ $T_{regs}$, a microbiota induced $T_{reg}$ lineage ($iT_{reg}$) with immense stability and immune resolving capabilities, were more than 2-fold increased in the colonic lamina propria of WD-MCB fed mice (FIG. 9A, p<0.001). This regulatory T cell phenotype is of particular interest during gut-specific immune responses, as they exhibit enhanced suppressive capacity during intestinal inflammation and mediate immunological tolerance to gut pathobionts, hence protecting against barrier dysfunction and subsequent colitis.

RORγt is the hallmark transcription factor for T helper type 17 (Th17) cells and accordingly essential for IL-17 production. We therefore investigated if the $Foxp3^+RORγt^+$ $_iT_{regs}$ were capable of secreting IL-17 upon stimulation. Stimulated iTregs expressed ample amounts of IL-17, while unstimulated cells, as expected, displayed hampered IL-17 expression (FIG. 9B). Gut-specific delivery of IL-17 has recently been shown to control metabolic disease and reduce obesity and insulin resistance in mice. It is therefore interesting to note, that not only did WD-MCB fed mice exhibit increased numbers of RORγt+ iT$_{regs}$ (FIG. 9A), but the proportion of IL-17+ cells within this cell subset were further ~2.5-fold increased in WD-MCB fed mice compared to WD-Macadamia fed mice (FIG. 9C-F, p>0.0001), thus pointing to improved glucoregulatory or anti-obesogenic effects.

Figure 9H:
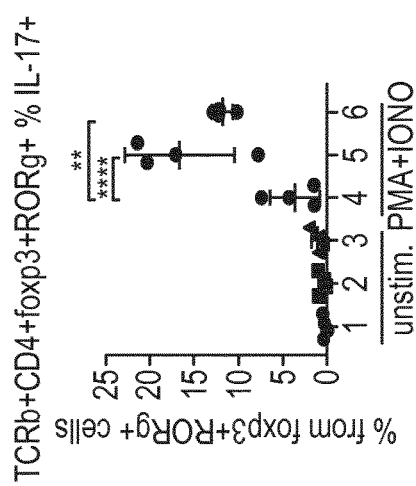
Figure 9G:
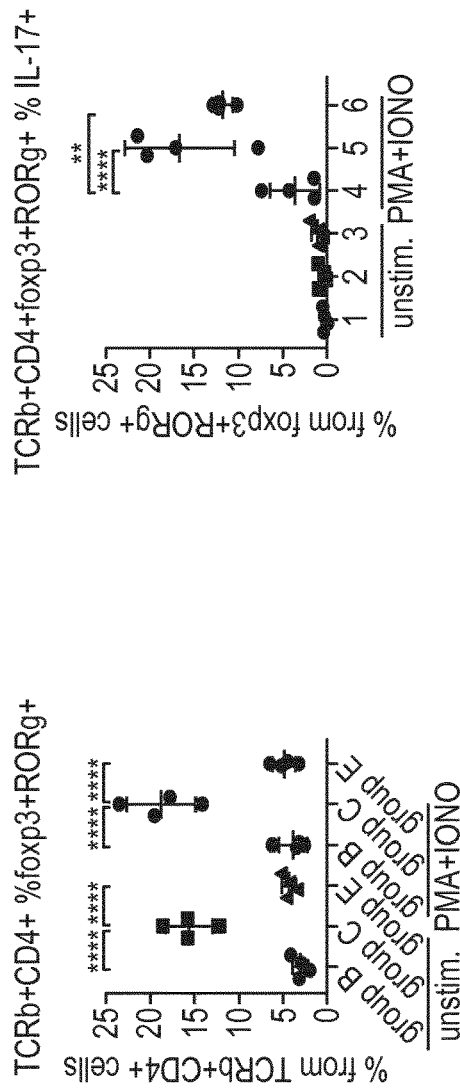
Figure 9L:
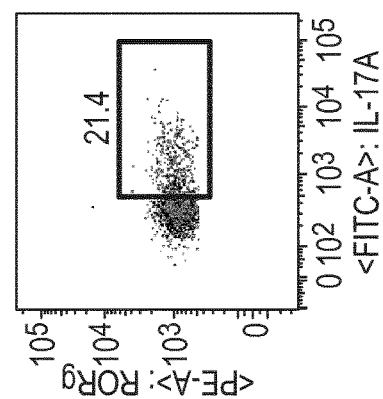
Figure 9K:
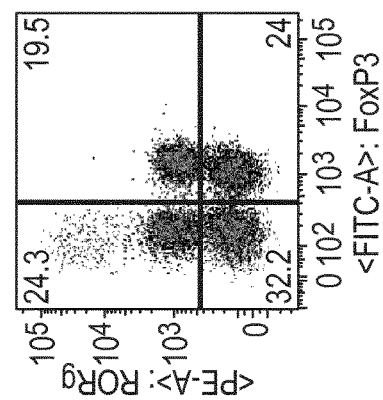
Figure 9J:
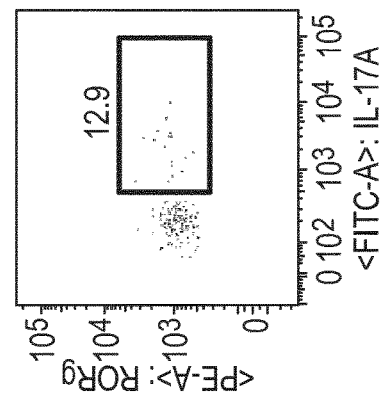
Figure 9I:
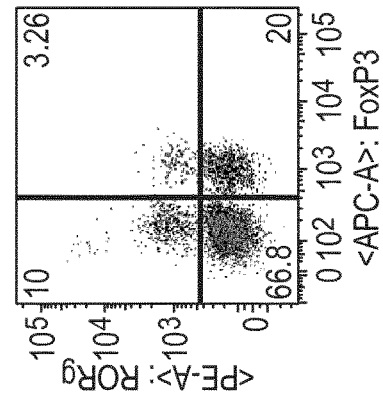

We further observed a similar phenotype in the small intestine of experimental mice (FIG. 9G-L), where RORγt+ iT$_{regs}$ in WD-MCB fed mice reached a ~4-5-fold increase compared to WD-Macadamia fed control mice (FIG. 9G, p<0.0001).

Gut residing IL-17+ T cells have been shown to be important for anti-obesogenic phenotypes, whereas liver-expressed IL-17 is detrimental for hepatic lipid and glucose regulation. As such, we next evaluated if the potent immune profile in the intestines exhibited spill-over to the liver or if it was restricted to the gastrointestinal cavity. We therefore analysed the liver of the experimental mice by H&E stain. Mice fed WD-MCB unveiled diminished NAFLD-activity compared to mice fed WD-Macadamia (FIG. 9M-N, p<0.01), suggesting that the increased IL-17 expression in WD-MCB fed mice was restricted to gut-specific iT$_{regs}$.

Thus, it may be seen from these data that WD-MCB feeding stimulates induction of gut-specific regulatory T cells and this may contribute to improved glucoregulatory or anti-obesogenic effects.

The invention claimed is:

1. A method for treatment of gastrointestinal (GI) tract dysbiosis in a mammalian subject having a perturbed GI tract microbiota profile, said method comprising administering an effective, dysbiosis improving amount of a non-viable *Methylococcus capsulatus* or a lysate of *Methylococcus capsulatus* as a pharmaceutically active ingredient to said mammalian subject.

2. The method of claim 1, wherein said treatment normalises the perturbed GI tract microbiota profile or maintains a normal GI tract microbiota profile in the subject, said method comprising administering an amount of the non-viable *Methylococcus capsulatus* or the lysate of *Methylococcus capsulatus* to the subject which is effective to normalise a perturbed GI tract microbiota profile of the subject or to maintain a normal GI tract microbiota profile of the subject.

3. The method of claim 1, wherein said non-viable *Methylococcus capsulatus* has been rendered non-viable by irradiation or thermally.

4. The method of claim 1, wherein said lysate has been prepared by mechanical means, hydrolysis, autolysis or combination thereof.

5. The method of claim 4, wherein said mechanical means for lysing *Methylococcus capsulatus* cells is selected from impact-based techniques, shear stress based techniques, hydrostatic pressure based techniques, cryopulverisation, nitrogen decompression and ultrasonic homogenisation.

6. The method of claim 5, wherein said lysate is prepared by a shear stress-based technique.

7. The method of claim 1, wherein said non-viable *Methylococcus capsulatus* or lysate of *Methylococcus capsulatus* is administered in drinking water, in a foodstuff or in a pharmaceutical composition.

8. The method of claim 6, wherein the shear stress-based technique is a French pressure cell press.

* * * * *